US007563606B2

(12) United States Patent
Aoyama et al.

(10) Patent No.: US 7,563,606 B2
(45) Date of Patent: Jul. 21, 2009

(54) METHOD FOR PRODUCING NON-AMINO ORGANIC ACID

(75) Inventors: Ryusuke Aoyama, Yokohama (JP); Makoto Murase, Yokohama (JP); Kenji Yamagishi, Yokohama (JP); Kiyohiko Nishi, Kawasaki (JP); Hiroyuki Kojima, Kawasaki (JP)

(73) Assignees: Mitsubishi Chemical Corporation, Tokyo (JP); Ajinomoto Co., Inc., Tokyo (JP)

( * ) Notice: Subject to any disclaimer, the term of this patent is extended or adjusted under 35 U.S.C. 154(b) by 328 days.

(21) Appl. No.: 11/376,133

(22) Filed: Mar. 16, 2006

(65) Prior Publication Data

US 2006/0281156 A1 Dec. 14, 2006

Related U.S. Application Data

(63) Continuation of application No. PCT/JP2004/013658, filed on Sep. 17, 2004.

(30) Foreign Application Priority Data

Sep. 17, 2003 (JP) ............................ 2003-324277

(51) Int. Cl.
*C12P 7/46* (2006.01)
*C12P 7/44* (2006.01)
*C12P 7/66* (2006.01)

(52) U.S. Cl. ....................... 435/145; 435/135; 435/142; 435/252.3

(58) Field of Classification Search ....................... None
See application file for complete search history.

(56) References Cited

U.S. PATENT DOCUMENTS

| | | | |
|---|---|---|---|
| 5,034,105 | A | 7/1991 | Berglund et al. |
| 5,132,456 | A | 7/1992 | King et al. |
| 5,142,834 | A | 9/1992 | Laclave |
| 5,143,833 | A | 9/1992 | Datta |
| 5,143,834 | A | 9/1992 | Glassner et al. |
| 5,168,055 | A | 12/1992 | Datta et al. |
| 5,504,004 | A | 4/1996 | Guettler |
| 5,770,435 | A | 6/1998 | Donnelly et al. |
| 5,869,301 | A | 2/1999 | Nghiem et al. |
| 5,958,744 | A | 9/1999 | Berglund et al. |
| 6,265,190 | B1 | 7/2001 | Yedur et al. |
| 6,448,061 | B1 | 9/2002 | Pan et al. |
| 6,455,284 | B1 | 9/2002 | Gokarn et al. |
| 2002/0150999 | A1 | 10/2002 | Dusch et al. |
| 2002/0197605 | A1 | 12/2002 | Nakagawa et al. |
| 2003/0017559 | A1 | 1/2003 | Donnelly et al. |
| 2003/0069354 | A1 | 4/2003 | Oyasato et al. |
| 2003/0087381 | A1 | 5/2003 | Gokarn et al. |
| 2003/0100079 | A1 | 5/2003 | Mockel et al. |
| 2005/0196848 | A1 | 9/2005 | Dusch et al. |
| 2006/0172401 | A1 | 8/2006 | Yamagishi |
| 2006/0205048 | A1 | 9/2006 | Murase et al. |
| 2006/0228712 | A1 | 10/2006 | Nakagawa et al. |
| 2006/0276674 | A1 | 12/2006 | Kushiku et al. |
| 2007/0154999 | A1 | 7/2007 | Fukui et al. |

FOREIGN PATENT DOCUMENTS

| | | |
|---|---|---|
| CA | 2322553 | 4/2001 |
| EP | 0 389 103 | 9/1990 |
| EP | 1 096 013 | 5/2001 |
| EP | 1 108 790 | 6/2001 |
| EP | 1 748 062 | 1/2007 |
| JP | 61-209596 | 9/1986 |
| JP | 62-048394 | 3/1987 |
| JP | 62-238231 | 10/1987 |
| JP | 62-238232 | 10/1987 |
| JP | 62-294090 | 12/1987 |
| JP | 2-283289 | 11/1990 |
| JP | 3-072891 | 3/1991 |
| JP | 3-151884 | 6/1991 |
| JP | 5-260985 | 10/1993 |
| JP | 6-14781 | 1/1994 |
| JP | 7-67683 | 3/1995 |
| JP | 7-304839 | 11/1995 |
| JP | 11-113588 | 4/1999 |
| JP | 11-130852 | 5/1999 |
| JP | 11-196887 | 7/1999 |
| JP | 11-196888 | 7/1999 |
| JP | 11-206385 | 8/1999 |
| JP | 2000-500333 | 1/2000 |
| JP | 2000-037196 | 8/2000 |
| JP | 2001-161386 | 6/2001 |
| JP | 2001-190297 | 7/2001 |
| JP | 2001-514900 | 9/2001 |

(Continued)

OTHER PUBLICATIONS

English Language Abstract of JP 2003-235592.

(Continued)

*Primary Examiner*—Herbert J. Lilling
(74) *Attorney, Agent, or Firm*—Greenblum & Bernstein, P.L.C.

(57) ABSTRACT

Non-amino organic acids such as succinic acid, malic acid and fumaric acid are produced by reacting bacterial cells or treated bacterial cells of a coryneform bacterium with an organic raw material in an aqueous medium containing magnesium carbonate and/or magnesium hydroxide, and a certain range of concentration of a monovalent cation, while maintaining the pH within a certain range without increasing the volume of the aqueous medium.

10 Claims, 5 Drawing Sheets

FOREIGN PATENT DOCUMENTS

| | | |
|---|---|---|
| JP | 2002-511250 | 4/2002 |
| JP | 2002-191370 | 7/2002 |
| JP | 2002-291477 | 10/2002 |
| JP | 2003-171448 | 6/2003 |
| JP | 2003-199522 | 7/2003 |
| JP | 2003-235592 | 8/2003 |
| JP | 2003-235593 | 8/2003 |
| WO | 97/16528 | 5/1997 |
| WO | 99/06532 | 2/1999 |
| WO | 99/09196 | 2/1999 |
| WO | 99/53035 | 10/1999 |
| WO | 01/66508 | 9/2001 |
| WO | 02/29020 | 4/2002 |
| WO | 02/36797 | 5/2002 |
| WO | 02/072855 | 9/2002 |
| WO | 03/040290 | 5/2003 |
| WO | 2005/005649 | 1/2005 |
| WO | 2005/021770 | 3/2005 |
| WO | 2005/030973 | 4/2005 |
| WO | 2005/113744 | 12/2005 |
| WO | 2005/113745 | 12/2005 |

OTHER PUBLICATIONS

English Language Abstract of JP 11-196888.
English Language Abstract of JP 2003-199522.
English Language Abstract of JP 3-072891.
English Language Abstract of JP 2000-037196.
English Language Abstract of JP 11-113588.
Guettler et al., International Journal of Systematic Bacteriology 49: 207-216 (1999).
Millard et al., Applied and Environmental Microbiology 62(5):1808-1810 (1996).
Hong and Lee, Biotechnology and Bioengineering, 74(2): 89-95 (2001).
U.S. Appl. No. 11/561,011 (Fukui et al.), filed Nov. 17, 2006.
English Language Abstract and translation of JP 11-196887, Jul. 1999.
English Language Abstract and translation of JP 2002-291477, Oct. 2002.
English Language Abstract and translation of JP 2003-235593, Aug. 2003.
English Language Abstract of JP 5-260985, Oct. 1993.
English Language Abstract of JP 62-048394, Mar. 1987.
English Language Abstract of JP 61-209596, Sep. 1986.
English Language Abstract of JP 11-206385, Aug. 1999.
English Language Abstract of JP 7-304839, Nov. 1995.
English Language Abstract of JP 7-67683, Mar. 1995.
English Language Abstract of JP 11-130852, Aug. 1999.
English Language Abstract of JP 2003-171448, Jun. 2003.
English Language Abstract of JP 2002-191370, Jul. 2002.
English Language Abstract of JP 6-14781, Jan. 1994.
English Language Abstract of JP 2001-161386, Jun. 2001.
English Language Abstract of JP 62-238231, Oct. 1987.
English Language Abstract of JP 62-238232, Oct. 1987.
English Language Abstract of JP 2001-190297, Apr. 2002.
Bott et al. *Journal of Biotechnology* 104:129-153 (2003).
Goldberg et al. *Applied and Environmental Microbiology* 45(6):1838-1847 (1983).
Kurokawa et al. *Arch. Microbiol*. 183:317-324 (2005).
Schnorpfeil et al. *Eur. J. Biochem*. 268:3069-3074 (2001).
Branden et al. Introduction to Protein Structure, Garland Publishing Inc., New York, p. 247, 1991.
Witkowski et al. *Biochemistry* 38:11643-11650 (1999).
Seffernick et al. *J. Bacteriol*. 183(8):2405-2410 (2001).
Ba et al. *Biomacromolecules* 4:1827-1834 (2003).
Gokarn et al. *Biotechnology Letters* 20(8):795-798 (1998).
Hong et al. *Appl. Microbiol. and Biotechnol*. 58:286-290 (2002).
Gokarn et al. *Applied and Environmental Microbiology* 66(5):1844-1850 (2000).
Gokarn et al. *Appl. Microbiol. Biotechnol*. 56:188-195 (2001).
Lin et al. *Applied Genetics and Molecular Biotechnology*, published online: Nov. 24, 2004, total pages: 16.
Mat-Jan et al. *Journal of Bacteriology*, 171.(1):342-348 (1989).
Stols et al. *Applied and Environmental Microbiology* 63(7):2695-2701 (1997).
Wang et al. *Applied Biochemistry and Biotechnology* 70-72:919-928 (1998).
Zeikus et al. *Appl. Microbiol. Biotechnol*. 51:545-552 (1999).
Gong et al. *Applied Biochemistry and Biotechnology* 57/58:481-487 (1996).
Mori et al. *Shokuhin to Kagaku* 44(4):43-49 (2002).
Reinscheid et al., *Microbiology* 145:503-513 (1999).
Kalinowski et al. *J. of Biotech*. 104(1-3):5-25 (2003).
Inui et al. *J. of Mol. Microbiol. and Biotechnol*. 7(4):182-196 (2004).
Kirchner et al. *J. of Biotech*. 104(1-3):287-299 (2003).
Chotani et al. *Biochimica et Biophysica Acta* 1543(2):434-455 (2000).
Maxa et al. *Mitteilungen Klosterneuenburg* 41(6):233-237 (1991).
Calvary et al. *Microchemical Journal* 23(4):473-480 (1978).
Database UniProt, "Acetyl-CoA Hydrolase", Accession No. Q8NMK4, Oct. 1, 2002.
Database EPO Proteins, "Sequence 32 from International Publication No. WO 03/040290", Accession No. AX771820, Jul. 2, 2003.
Database EMBL, "Sequence 31 from International Publication No. WO 03/040290", Accession No. AX771819, Jul. 2, 2003.
Database Geneseq, "C-Glutamicum Protein Fragment SEQ ID No. 6326", Accession No. AAG92572, Sep. 26, 2001.
Database EMBL, "Sequence 2826 from EP 1 108 790", Accession No. AX122910, May 10, 2001.
Database UniProt, "Butyryl-CoA: Acetate Coenzyme A Transferase", Accession No. Q6M2R3, Jul. 5, 2004.
KEGG Database on-line, NCg10359, 2006.
KEGG Database on-line, NCg10360, 2006.
KEGG Database on-line, NCg10361, 2006.
NP_601767, NCBI Sequence Viewer, Acetyl-CoA hydrolase, Pub. Date Mar. 20, 2002.
NP_601811, NCBI Sequence Viewer, Pyruvate Dehyrogenase, Pub. Date Mar. 20, 2002.

METHOD FOR PRODUCING NON-AMINO ORGANIC ACID

CROSS-REFERENCE TO RELATED APPLICATION

This is a continuation of International Application No. PCT/JP2004/013658, filed Sep. 17, 2004, the contents of which are expressly incorporated by reference herein in its entirety.

TECHNICAL FIELD

The present invention relates to a production of a non-amino organic acid using coryneform bacteria.

BACKGROUND ART

For the production of non-amino-organic acids including succinic acid by fermentation, anaerobic bacteria including those belonging to the genus *Anaerobiospirillum* or *Actinobacillus* are usually used (U.S. Pat. Nos. 5,142,834 and 5,504,004, and International Journal of Systematic Bacteriology (1999), 49, 207-216). Although the yield of products is high by using such anaerobic bacteria, many nutrients are required for their proliferation, and therefore, it is necessary to add a large amount of organic nitrogen sources such as corn steep liquor (CSL) into a culture medium. The addition of large amount of organic nitrogen sources not only leads to an increase in the culture cost but also an increase in purification cost for isolating the product, therefore it is not economical.

In addition, methods in which aerobic bacteria such as coryneform bacteria are cultured under aerobic conditions to proliferate bacterial cells and then harvested and washed to allow them as resting cells to produce non-amino organic acid without oxygen aeration, have been known (JP11-113588A and JP11-196888A). These methods are economical because bacteria can grow sufficiently in a simple culture medium containing less amount of organic nitrogen for proliferating bacterial cells. However, there is still a desire for improvement in terms of production amount, concentration, and production rate of the target organic acids per bacterial cell as well as simplification of production process, and so on.

In the case of producing non-amino organic acids by fermentation, pH decreases along with generation of the non-amino organic acids, so that it is necessary to perform the reaction while adjusting pH by neutralization. So far, sodium carbonate, ammonium carbonate, or the like has been used for adjusting pH, but there has been a problem that the volume of the reaction solution increases by addition of a neutralizing solution. Meanwhile, because magnesium carbonate and magnesium hydroxide are difficult to be dissolved in water, they have not been used for adjusting the pH in production of non-amino organic acids by fermentation using coryneform bacteria.

DISCLOSURE OF THE INVENTION

An object of the present invention is to provide a method for more efficiently producing non-amino organic acids by fermentation while adjusting the pH of a fermentation solution within a certain range.

The inventors of the present invention have made extensive studies for solving the above-mentioned object. As a result, they found that non-amino organic acids can be produced while preventing the increase in the volume of the aqueous medium during the fermentation and maintaining the pH of the medium within a certain range, by reacting a coryneform bacterium with an organic raw material in an aqueous medium while neutralizing the aqueous medium with magnesium carbonate and/or magnesium hydroxide. Moreover, they found that the consumption rate of the organic raw material, production rate and yield of the organic acid can be increased by adding a monovalent cation in the aqueous medium. Based on these findings, the present invention has been completed.

That is, according to the present invention, the following inventions are provided.

(1) A method for producing a non-amino organic acid from an organic raw material, comprising reacting bacterial cells or treated bacterial cells of a coryneform bacterium with the organic raw material in an aqueous medium and collecting the non-amino organic acid, wherein the bacterial cells or the treated bacterial cells are allowed to react with the organic raw material while neutralizing the aqueous medium with magnesium carbonate and/or magnesium hydroxide.

(2) A method for producing a non-amino organic acid from an organic raw material, comprising reacting bacterial cells or treated bacterial cells of a coryneform bacterium with the organic raw material in an aqueous medium containing a monovalent cation and collecting the non-amino organic acid, wherein the bacterial cells or the treated bacterial cells are allowed to react with the organic raw material while neutralizing the aqueous medium with magnesium carbonate and/or magnesium hydroxide.

(3) The method according to (2), wherein the monovalent cation is an ammonium ion or a sodium ion.

(4) The method according to any one of (1) to (3), wherein the bacterial cells or the treated bacterial cells are allowed to react with the organic raw material under anaerobic atmosphere.

(5) The method according to any one of (1) to (4), wherein the aqueous medium comprises a carbonate ion, a bicarbonate ion, or carbon dioxide gas.

(6) The method according to any one of (1) to (5), wherein the organic raw material is glucose or sucrose.

(7) The method according to any one of (1) to (6), wherein the non-amino organic acid is succinic acid, malic acid, or fumaric acid.

(8) The method according to any one of (1) to (7), wherein the coryneform bacterium is modified to decrease a lactate dehydrogenase activity to not more than 10% as compared to an unmodified strain.

(9) The method according to any one of (1) to (7), wherein the coryneform bacterium is modified to enhance an activity of fumarate reductase and/or pyruvate carboxylase.

(10) The method according to any one of (1) to (7), wherein the coryneform bacterium is modified to decrease a lactate dehydrogenase activity to not more than 10% as compared to an unmodified strain and enhance an activity of fumarate reductase and/or pyruvate carboxylase.

(11) A method of producing a polymer containing a non-amino organic acid, which comprises producing a non-amino organic acid by the method according to any one of (1) to (10) and performing a polymerization reaction using the obtained non-amino organic acid as a raw material.

DESCRIPTION OF THE PREFERRED EMBODIMENTS

Figure 1:
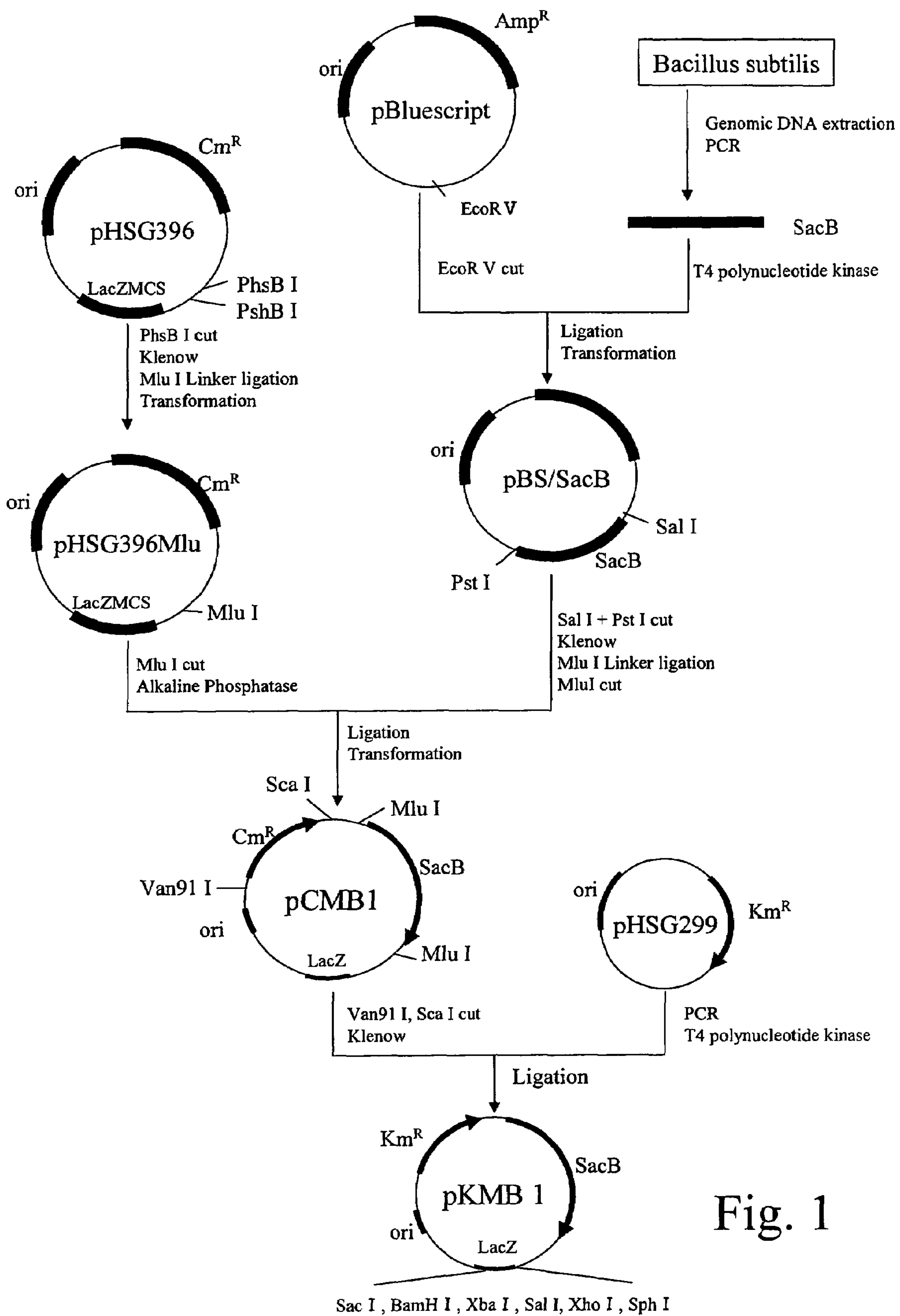
FIG. 1 shows a procedure for constructing the plasmid pKMB1 and a restriction enzyme map thereof.

Hereinafter, embodiments of the present invention will be described in detail.

The production method of the present invention is a method for producing a non-amino organic acid from an organic raw material, comprising reacting bacterial cells or treated bacterial cells of a coryneform bacterium with the organic raw material in an aqueous medium and collecting the non-amino organic acid, wherein the bacterial cells or the treated bacterial cells are allowed to react with the organic raw material while neutralizing the aqueous medium with magnesium carbonate and/or magnesium hydroxide.

A coryneform bacterium to be used in the present invention is not particularly limited as long as it has an ability to produce a non-amino organic acid. However, examples of the coryneform bacterium include those belonging to the genus *Corynebacterium, Brevibacterium*, or *Arthrobacter*. Of those, one belonging to the genus *Corynebacterium* or *Brevibacterium* is preferable. A bacterium belonging to *Corynebacterium glutamicum, Brevibacterium flavum, Brevibacterium ammoniagenes*, or *Brevibacterium lactofermentum* is more preferable.

Particularly preferable specific examples of the microorganism include *Brevibacterium flavum* MJ-233 (FERM BP-1497), *Brevibacterium flavum* MJ-233 AB-41 (FERM BP-1498), *Brevibacterium ammoniagenes* ATCC6872, *Corynebacterium glutamicum* ATCC31831, and *Brevibacterium lactofermentum* ATCC13869.

*Brevibacterium flavum* MJ-233 has been deposited as the accession number FERM P-3068 at National Institute of Bioscience and Human Technology, Agency of Industrial Science and Technology, Ministry of International Trade and Industry (currently International Patent Organism Depositary, National Institute of Advanced Industrial Science and Technology at Tsukuba Central 6, 1-1, Higashi 1-chome, Tsukuba-shi, Ibaraki-ken 305-8566, Japan) on Apr. 28, 1975, and then converted to an international deposit under Budapest Treaty on May 1, 1981 with the accession number FERM BP-1497.

*Brevibacterium flavum* may be currently classified into *Corynebacterium glutamicum* (Lielbl, W., Ehrmann, M., Ludwig, W. and Schleifer, K. H., International Journal of Systematic Bacteriology, 1991, vol. 41, p255-260). Therefore, in the present invention, *Brevibacterium flavum* MJ-233 and its mutant strain, MJ-233 AB-41, are defined as the same strains as *Corynebacterium glutamicum* MJ-233 and *Corynebacterium glutamicum* MJ-233 AB-41, respectively.

The above-mentioned bacteria used in the method of the present invention may be any strains including variant strains obtained by conventional treatments for mutagenesis, such as UV irradiation and NTG treatment, and recombinant strains bred by genetic procedures such as cell fusion and genetic recombination techniques, as well as wild-type strains. Furthermore, hosts for the genetic recombinant strains may be those classified in the same genus and species or those classified in different genus and species with respect to a parent strain, so long as it is a transformable microorganism, but preferably the host may be aerobic bacteria as described above.

In the production method of the present invention, a mutant strain modified to decrease lactate dehydrogenase activity is preferably used. Here, the term "lactate dehydrogenase activity is decreased" means a decrease in lactate dehydrogenase activity per bacterial cell as compared to a strain without modification in lactate dehydrogenase. The lactate dehydrogenase activity per bacterial cell is preferably decreased to not more than 10% as compared to a strain without modification in lactate dehydrogenase. The lactate dehydrogenase activity may be completely eliminated. The decrease in lactate dehydrogenase activity can be confirmed by determining lactate dehydrogenase activity by a known method (L. Kanarek and R. L. Hill, J. Biol. Chem. 239, 4202 (1964)). As a specific method for producing a mutant strain of a coryneform bacterium in which lactate dehydrogenase activity is decreased, for example, a method using homologous recombination on a chromosome as described in JP 11-206385 A or a method using a SacB gene described in the Examples of the present specification (Schafer, A. et al., Gene 145 (1994) 69-73) can be used.

Meanwhile, in the production method of the present invention, a coryneform bacterium modified to enhance the activity of fumarate reductase (FRD) and/or pyruvate carboxylase (PC) may also be used. Herein, the term "enhance" means that the activities of these enzymes per bacterial cell increase as compared to an unmodified strain. With regard to fumarate reductase, fumarate reductase of *Escherichia coli* is an enzyme that functions in a reverse reaction of succinate dehydrogenase that acts in the forward direction in TCA cycle. It is known that the enzyme is involved in fumarate respiration under anaerobic conditions, and the gene expression thereof is suppressed under aerobic conditions at a transcriptional level (Jones, H. M., Gunsalus, R. P., J. Bacteriol., 1985, Vol. 164, p 1100-1109). Therefore, growth of bacterial cells may be deteriorated if the activity of fumarate reductase is excessively enhanced, so, in the present invention, it is preferable that the fumarate reductase activity is enhanced to such an extent that growth of bacterial cells is not significantly inhibited.

The enhancement of the activities of PC and FRD may be confirmed by measuring the activities of these enzymes by the methods as described below for measuring a decrease in NADH or decrease in $K_3Fe(CN)_6$, respectively. A coryneform bacterium modified so as to enhance expression of fumarate reductase or pyruvate carboxylase can be prepared by highly expressing the fumarate reductase (FRD) or pyruvate carboxylase (PC) gene using a gene recombination technology in the same way as described in JP 11-196888 A.

The PC gene used in the method of the present invention may be a gene whose nucleotide sequence is already known. Alternatively, a gene obtained by isolating a DNA fragment encoding a protein having the PC activity from a chromosome of a microorganism, animal, plant, or the like by such a method as described below, and determining its nucleotide sequence can be used. Furthermore, after the determination of the nucleotide sequence, a gene synthesized based on the sequence can also be used.

DNA fragments containing PC genes reside on a chromosome of microorganisms, animals, and plants. Basic procedures for preparing a PC gene from those donor microorganisms, animals, or plants are explained below by referring to a gene derived from coryneform bacteria whose sequence is known.

The PC gene resides on the chromosome of *Corynebacterium glutamicum* ATCC13032, which is one of coryneform bacteria, (Peters-Wendisch, P. G. et al., Microbiology, vol. 144 (1998) p 915-927), and its nucleotide sequence is known (GenBank Database Accession No. AP005276) (SEQ ID NO: 15), so that the gene can be isolated and obtained by PCR.

For instance, the PC gene of about 3.7 kb can be amplified by carrying out PCR using oligonucleotides having nucleotide sequences shown in SEQ ID NOS: 13 and 14 as primers and using chromosome of *Corynebacterium glutamicum* as a template. In this case, an appropriate restriction enzyme recognition site may be added to the 5'-terminal of the primers used in PCR to allow the gene to be inserted into a suitable region of such a vector as described below, and the obtained recombinant vector can be used for gene transfer into coryneform bacterium.

In addition, even if a nucleotide sequence is unidentified, a protein can be purified based on PC activity and a probe is then synthesized based on the N-terminal amino acid sequence of the protein or a sequence of partially-digested fragments to isolate a gene fragment by routine hybridization procedures. Alternatively, a probe or primer may be synthesized on the basis of an amino acid sequence in a region conserved in PC proteins to obtain a fragment by hybridization or PCR. The nucleotide sequence of the obtained fragment can be determined by a conventional method.

In the present specification, the size of the digested DNA fragments and plasmids can be calculated; when agarose gel electrophoresis is employed, on the basis of a reference line drawn by migration distances of DNA fragments having known molecular weights obtained by digestion of *Escherichia coli* λ phage with the restriction enzyme HindIII on the same agarose gel; or when polyacrylamide gel electrophoresis is employed, on the basis of a reference line drawn by migration distances of DNA fragments having known molecular weights obtained by digestion of *Escherichia coli* φX174 phage with the restriction enzyme HaeIII on the same polyacrylamide gel. For the determination of the size of each of the DNA fragments, 1% agarose gel electrophoresis was employed for the fragments of not less than 1 kb in size, and 4% polyacrylamide gel electrophoresis was employed for the fragments of about 0.1 kb or more but less than 1 kb in size.

The DNA fragment containing the above-described PC gene used in the present invention may be isolated from the chromosomal DNA of *Corynebacterium glutamicum*, or synthesized using an ordinarily used DNA synthesizing apparatus, for example, a 394 DNA/RNA synthesizer manufactured by Applied Biosystems Inc. Furthermore, in the PC gene obtained from the chromosomal DNA of a coryneform bacterium as described above, some nucleotides may be replaced by other nucleotides, or deleted, or additional nucleotides may be inserted, in the nucleotide sequence of SEQ ID NO: 15, as long as there is no substantial defect in functions of the encoded PC, i.e., the properties involved in carbon dioxide fixation. Furthermore, part of the nucleotide sequence may be inverted. Any of those derivatives can be used in the present invention. For example, a DNA that hybridizes with a DNA having a nucleotide sequence of SEQ ID NO: 15 under stringent conditions, or a DNA having a homology of not less than 90%, preferably not less than 95%, or more preferably not less than 99% to the nucleotide sequence of SEQ ID NO: 15, and encodes a protein having the PC activity, can also be preferably used. Here, the stringent conditions include a condition that allows hybridization at salt concentrations corresponding to 60° C., 1×SSC, 0.1% SDS, preferably 0.1×SSC, 0.1% SDS, which is a washing condition of a conventional Southern hybridization.

The PC gene obtained from any bacteria other than *Corynebacterium glutamicum*, or from any microorganisms, animals, and plants can also be used. In particular, the nucleotide sequence of the PC genes from the microorganisms, animals, and plants, such as those described below, are known (references are indicated below). Therefore, the PC gene can be obtained in the same way as described above with hybridization or the amplification of ORF by PCR. The obtained gene may be inserted downstream of the TZ4 promoter in the vector prepared in Example 3 as shown below. An aerobic coryneform bacterium is transformed with the inserted plasmid in accordance with the method as described in Example 4 (C), and the bacterium can be used for producing a non-amino organic acid.

*Homo sapiens* [Biochem. Biophys. Res. Comm., 202, 1009-1014, (1994)]

*Mus musculus* [Proc. Natl. Acad. Sci. USA., 90, 1766-1779, (1993)]

*Rattus norvegicus* [GENE, 165, 331-332, (1995)]

Yeasts; *Saccharomyces cerevisiae* [Mol. Gen. Genet., 229, 307-315, (1991)]

*Schizosaccharomyces pombe* [DDBJ Accession No.; D78170]

*Bacillus stearothermophilus* [GENE, 191, 47-50, (1997)]

*Rhizobium etli* [J. Bacteriol., 178, 5960-5970, (1996)]

The DNA fragment containing the PC gene can be expressed by inserting the DNA fragment into a suitable expression plasmid such as pUC118 (manufactured by Takara Shuzo Co., Ltd.), followed by introduction into a suitable host microorganism such as *Escherichia coli* JM109 (available from Takara Shuzo Co., Ltd.). The expressed PC gene product, pyruvate carboxylase (SEQ ID NO: 16), can be confirmed by directly determining the PC activity by the method of Magasanik [J. Bacteriol., 158, 55-62, (1984)] using a crude enzyme solution prepared from the transformant, and then comparing the PC activity with that of a crude enzyme solution prepared from a non-transformant.

The DNA fragment containing the PC gene is inserted into a suitable plasmid, such as a plasmid vector containing at least a gene responsible for replication and amplification of the plasmid in coryneform bacteria, and thereby, a recombinant plasmid capable of high expression of PC in coryneform bacteria can be obtained. In the recombinant plasmid, a promoter for expressing the PC gene may be one derived from coryneform bacteria. However, it is not limited to such promoters, and any promoter can be used so long as it is a nucleotide sequence capable of initiating the transcription of the PC gene. For instance, TZ4 promoter as described in Example 3 may be used.

A plasmid vector, into which the PC gene can be introduced, is not specifically limited so long as it contains a gene responsible for replication and amplification in coryneform bacterium. The specific examples include: plasmid pCRY30 described in JP03-210184A; plasmids pcRY21, pCRY2KE, pCRY2KX, pCRY31, pCRY3KE, and pCRY3KX described in JP02-72876A and U.S. Pat. No. 5,185,262; plasmids pCRY2 and pCRY3 described in JP-01-91686A; pAM330 described in JP58-67769A; pHM1519 described in JP58-77895A; pAJ655, pAJ611, and pAJ1844 described in JP58-192900A; pCG1 described in JP57-134500A; pCG2 described in JP58-35197A; and pCGG4 and pCG11 described in JP57-183799A.

Of those, plasmids comprising a gene responsible for replication and amplification and a gene responsible for the stabilization of the plasmid in coryneform bacteria are preferably used as plasmid vectors for the host-vector system in coryneform bacterium. For instance, plasmids pCRY30, pCRY21, pCRY2KE, pCRY2KX, pCRY31, pCRY3KE, and pCRY3KX can be preferably used.

A coryneform bacterium having enhanced PC gene expression to be used in the present invention is obtained by transforming a coryneform bacterium, for example, *Brevibacterium flavum* MJ-233 (FERM BP-1497) with a recombinant vector prepared by inserting the PC gene into an appropriate site of a plasmid vector which can be replicable in an aerobic coryneform bacterium. In addition, the enhancement of PC activity can also be performed by introducing, substituting, or amplifying the PC gene on a chromosome by means of a known homologous recombination method to thereby cause high expression of the gene. The transformation can be carried out by, for example, the electric pulse method (Res. Microbiol., Vol. 144, p. 181-185, 1993).

A bacterium in which the FRD activity is enhanced and which is used in the present invention may be obtained by introducing the FRD gene into a bacterium. The FRD gene is not particularly limited as long as it encodes a protein having the fumarate reductase activity, and examples thereof include a gene that is derived from *Escherichia coli* and has the nucleotide sequence shown in SEQ ID NO: 19. The gene is an operon gene containing genes (440 to 2,245, 2,241 to 2,975, 2,986 to 3,381, and 3,392 to 3,751 of SEQ ID NO: 19) that encode 4 subunits (frdA, frdB, frdc, and frdD; SEQ ID NOS: 20 to 23) that constitute FRD. The full length of the gene may be introduced into a bacterium, or the subunit genes may be separately introduced. Each subunit gene may be a DNA that hybridizes with a DNA having the above-described nucleotide sequence under stringent conditions or may be a homolog having homology of not less than 90%, preferably not less than 95%, more preferably not less than 99% to the above-described nucleotide sequence as long as it encodes a subunit protein that can form a complex having the FRD activity. Herein, examples of the stringent conditions include a condition of hybridization at 60° C. at a salt concentration corresponding to 1×SSC and 0.1% SDS, preferably 0.1×SSC and 0.1% SDS, which are washing conditions for conventional Southern hybridization. Among such FRD gene homologs, preferable is one that encodes a protein in which an amino acid corresponding to the amino acid at position 17 in the B subunit (frdB) (SEQ ID NO: 21) is lysine. A gene having the nucleotide sequence shown in SEQ ID NO: 19 or a homolog thereof may be obtained by the PCR method or hybridization method. If necessary, a mutation to replace the amino acid corresponding to the amino acid at position 17 in the frdB with lysine may be introduced by a known method.

Meanwhile, the FRD gene derived from a bacterium other than *Escherichia coli*, other microorganism, animal, or plant may also be used. As such a FRD gene derived from a microorganism, animal, or plant, a gene, which is obtained by isolating a gene that encodes a protein having the FRD activity from a chromosome of a microorganism, animal, plant, or the like based on the homology and followed by sequence determination, can be used. Furthermore, after the nucleotide sequence has been determined, a gene which is synthesized based on the sequence may also be used. These genes may be obtained by amplifying a region including the promoter and ORF by the hybridization method or PCR.

A recombinant plasmid that enables enhancement of FRD expression in a coryneform bacterium can be obtained by introducing the obtained DNA fragment containing the FRD gene into an appropriate plasmid, for example, a plasmid vector including at least a gene responsible for replication and amplification in a coryneform bacterium. The plasmid vector for introducing the FRD gene into a coryneform bacterium is not particularly limited as long as it contains a gene that controls a function of replication and amplification in a coryneform bacterium, and the above-described pCRY30, pCRY21, and the like may be used. The FRD activity may be enhanced by introducing, substituting, or amplifying the FRD gene on a chromosome by a known homologous recombination method to thereby cause high expression of the gene.

As described above, in the present invention, it is preferable that the fumarate reductase activity is enhanced to such an extent that growth of bacterial cells is not significantly inhibited, so that it is preferable that the expression level of the FRD gene is adjusted by selecting appropriate copy numbers of plasmids or by selecting a promoter having appropriate expression intensity. Herein, promoter for expressing the FRD gene may be any promoter as long as it functions in a coryneform bacterium, and a promoter of the FRD gene itself may also be used.

In the present invention, in the case of using a bacterium having enhanced activities of PC and FRD, these genes may be separately introduced into a bacterium or may be introduced simultaneously using a vector containing the both genes. In the present invention, it is particularly preferable to use a bacterium modified so as to decrease the lactate dehydrogenase activity and enhance the PC and/or FRD activity. For example, such bacterium may be obtained by preparing a coryneform bacterium having disrupted LDH gene and transforming the resultant bacterium with a recombinant vector containing the PC gene and FRD gene, respectively. Such modification procedures using the genes may be performed in any order.

When the above-described bacterium is used in the production method of the present invention, a bacterium subjected to slant culture on a solid medium such as an agar medium may be directly used for a reaction. However, it is preferable that the above-described bacterium is pre-cultured in a liquid medium before use (seed culture). A non-amino organic acid can be produced by reacting the bacterial cells obtained by seed-culture with an organic raw material while growing the bacterium in a medium containing the organic raw material. Alternatively, a non-amino organic acid can also be produced by reacting the proliferated bacterium cells with an organic raw material in an aqueous solution containing the organic raw material. For using an aerobic coryneform bacterium in the method of the present invention, it is preferable to use the bacterium after culturing it under a normal aerobic condition. The medium to be used for the culture may be any media normally used for the culture of microorganisms. For instance, a conventional medium, which is prepared by adding natural nutrient sources such as meat extract, yeast extract, or peptone to a composition comprising inorganic salts such as ammonium sulfate, potassium phosphate, and magnesium sulfate, may be used. The bacterial cells after culture are collected by centrifugation, membrane separation, or the like, and then used for the reaction.

In the present invention, treated bacterial cells may also be used. For instance, the treated bacterial cells include: bacterial cells immobilized on acrylamide, carageenan, or the like; bacterial cell extracts such as lysis product of bacterial cells, centrifugal supernatant thereof, and fraction obtained by partially purifying the supernatant with an ammonium sulfate treatment or the like.

An organic raw material to be used in the production method of the present invention is not limited as long as it is a carbon source which can be assimilated by the bacterium to produce a non-amino organic acid. Generally, fermentable carbohydrates including: carbohydrate such as galactose, lactose, glucose, fructose, glycerol, sucrose, saccharose, starch, and cellulose; polyalcohol such as glycerin, mannitol, xylitol, and ribitol can be used as a carbon source. Of those, glucose, sucrose, fructose, and glycerol are preferable, and glucose and sucrose are particularly preferable. In addition, a saccharified starch solution, molasses, or the like, which contains the above-mentioned fermentable carbohydrates, may also be used. Those fermentable carbohydrates may be used solely or in combination.

The concentration of the above-mentioned organic raw material is not particularly limited, but, it is advantageous to increase the concentration as high as possible within the range in which the production of a non-amino organic acid is not inhibited, and is generally in the range of 5 to 30% (w/v), preferably 10 to 20% (w/v). Furthermore, the organic raw materials may be supplemented along with a decrease in the organic raw material as the reaction progresses.

The aqueous medium to be used in the production method of the present invention is not particularly limited. Examples thereof include water, buffers, and liquid media, and preferable is a liquid medium as described above. Meanwhile, the aqueous medium used in the present invention preferably contains a nitrogen source, inorganic salt, and the like. Herein, the nitrogen source is not particularly limited as long as it is assimilated by the microorganism to produce a non-amino organic acid, and specific examples thereof include various organic or inorganic nitrogen compounds such as ammonium salts, nitrate salts, urea, soybean hydrolysate, casein degradation products, peptone, yeast extracts, meat extracts, and corn steep liquor. Examples of the inorganic salts to be used include various phosphate salts, sulfate salts, and metallic salts such as those of magnesium, potassium, manganese, iron, zinc, etc. If necessary, a growth-promoting factor including vitamins such as biotin, pantothenic acid, inositol, and nicotinic acid, nucleotides, and amino acids may also be added. Meanwhile, in order to suppress foaming in the reaction, an appropriate amount of a commercially available antifoam is preferably added to the aqueous medium.

In one embodiment of the production method of the present invention, the reaction is performed while neutralizing the aqueous medium by adding magnesium carbonate. Magnesium carbonate is present as $4MgCO_3.Mg(OH)_2.5H_2O$, which is relatively hard to be dissolved in water. Addition of magnesium carbonate to the aqueous medium may be performed by adding a solid such as a powder or a solution obtained by dissolving it in water or the like, but a solid such as a powder is preferably added as it is, because increase in the volume due to addition of a solution can be prevented. Even when an excessive amount of magnesium carbonate is added, the pH is maintained within a certain range without being too alkaline because of its low solubility of the powder. For example, in the case where an excessive amount of magnesium carbonate is added to a suspension liquid containing bacterial cells of a coryneform bacterium, the initial pH is about pH 8 to 8.5. Thereafter, the pH decreases along with the proceeding of the reaction, but the pH is maintained at about pH 6 to 7 even after the reaction. This may be because magnesium carbonate, which has been added in a large amount and is present as powder in the solution, is gradually dissolved and prevents drastic decrease in the pH.

In the other embodiment of the production method of the present invention, the reaction may be performed by neutralizing the aqueous medium by adding magnesium hydroxide. The magnesium hydroxide can be added to the aqueous medium in a form of a solid such as a powder or a solution obtained by dissolving it in water or the like. In this case, to increase the production amount of a target organic acid, the reaction is preferably performed while supplying carbon dioxide gas.

In the other embodiment of the production method of the present invention, the reaction may be performed by neutralizing the aqueous medium by adding magnesium carbonate and magnesium hydroxide. Addition of magnesium carbonate and magnesium hydroxide may be performed simultaneously to neutralize the medium. Alternatively, magnesium hydroxide may be added to neutralize the medium after addition of magnesium carbonate, or magnesium carbonate may be added to neutralize the medium after addition of magnesium hydroxide.

In the present reaction, the term "neutralization" means to maintain pH within a certain range, for example, pH 5 to 10, preferably pH 6 to 9.5 by reacting the non-amino organic acid produced by the reaction with magnesium carbonate and/or magnesium hydroxide. In the present invention, magnesium carbonate and/or magnesium hydroxide may be added at the beginning, and may also be supplemented during the reaction, if necessary. Meanwhile, in addition to magnesium carbonate and/or magnesium hydroxide, other pH-adjusting substances such as alkaline substances, carbonate salts, and urea may be added.

The aqueous medium preferably contains a carbonate or bicarbonate ion, or carbon dioxide gas, and then is allowed to react under an aerobic or anaerobic condition. The carbonate or bicarbonate ion is supplied from the magnesium carbonate which is used as a neutralizing agent. If necessary, the carbonate or bicarbonate ion may also be supplied from carbonic acid or bicarbonic acid or salts thereof or carbon dioxide gas. Specific examples of the salts of carbonate or bicarbonate include magnesium carbonate, ammonium carbonate, sodium carbonate, potassium carbonate, ammonium bicarbonate, sodium bicarbonate, and potassium bicarbonate. The carbonate ion or bicarbonate ion may be added at a concentration of 0.001 to 5 M, preferably 0.1 to 3 M, more preferably 1 to 2 M. When the carbon dioxide gas is introduced, the amount of the carbon dioxide gas is 50 mg to 25 g, preferably 100 mg to 15 g, more preferably 150 mg to 10 g per litter of the solution.

Meanwhile, the production rate or yield of an organic acid such as succinic acid can be increased by adding a monovalent cation to the aqueous medium to be used in the present invention. Examples of the monovalent cation include ammonium ion, sodium ion, and potassium ion, and among them, an ammonium ion is preferably used.

A monovalent cation can be added as a hydroxide of the monovalent cation such as ammonium hydroxide, sodium hydroxide, calcium oxide, or the like. However, it is preferable to be added as a salt of a monovalent cation. Examples of a salt of an ammonium ion include ammonium hydrogen carbonate, ammonium chloride, and ammonium sulfate. An example of a salt of a sodium ion includes sodium hydrogen carbonate. An example of a salt of a potassium ion includes potassium hydrogen carbonate.

When a salt of a monovalent cation is added, it is generally preferably added as a powder, suspension or solution. Moreover, when ammonium hydroxide is added, it may be added as ammonia water, or it may be added as gas being aerated to the reaction solution.

With regard to the addition concentration of a monovalent cation, the addition concentration of an ammonium ion is 0.001 M to 2 M, preferably 0.01 M to 1 M; the addition concentration of an sodium ion is 0.001 M to 2 M, preferably 0.01 M to 1 M; and the addition concentration of an potassium ion is 0.001 M to 2 M, preferably 0.01 M to 1 M.

The monovalent cation may be added at the beginning of the reaction, or may be continuously, gradually, or intermittently added during the reaction. In the case where the reaction solution is continuously used, the monovalent cation is preferably added so that the concentration of the monovalent cation in the reaction solution is within the above-described preferable concentration range in consideration of the amount of the monovalent cation that has been already added to the reaction solution.

The optimal temperature for the growth of the bacterium to be used in the present reaction is generally in the range of 25 to 35° C. On the other hand, the temperature during the production reaction is generally in the range of 25 to 40° C., preferably in the range of 30 to 37° C. The amount of bacterial cells used in the reaction is, but not limited to, 1 to 700 g/L, preferably 10 to 500 g/L, more preferably 20 to 400 g/L. The reaction duration is preferably 1 to 168 hours, more preferably 3 to 72 hours.

For culturing a bacterium, it is necessary to supply oxygen with aeration and agitation. On the other hand, although the production reaction may be performed with aeration and agitation, the production reaction may also be performed under anaerobic atmosphere where either aeration or oxygen supply is not provided, or aeration and oxygen supply is restricted. The term "anaerobic atmosphere" used herein means that a reaction is conducted while keeping the dissolved oxygen concentration in the solution to a low level. In this case, it is preferable to carry out a reaction at a dissolved oxygen concentration of 0 to 2 ppm, preferably 0 to 1 ppm, more preferably 0 to 0.5 ppm. For that purpose, for example, a method in which the reaction is carried out with no aeration in a hermetically-sealed vessel; a method in which the reaction is carried out while supplying an inert gas such as nitrogen gas; or a method in which the reaction is carried out while supplying an inert gas containing carbon dioxide gas, or a method in which the reaction is carried out with less stirring, may be performed.

In general, the reaction to produce an organic acid is completed at the time when an organic raw material such as glucose in a cultured medium is consumed. At this time, an organic acid such as succinic acid, malic acid, or fumaric acid is produced in the reaction solution. Of those, succinic acid is accumulated in a high level, and is preferable as a product.

The above-described reaction can yield an organic acid such as succinic acid, malic acid, or fumaric acid. A composition containing the organic acid itself is within a scope of the present invention. As the composition containing the organic acid, a composition including a high concentration of accumulated succinic acid is particularly preferable.

The organic acid that is accumulated in a reaction solution or culture solution may be separated and purified in accordance with a conventional method. Specifically, solids such as bacterial cells are removed by centrifugation, filtration, or the like, and then the resultant solution is desalted by means of an ion-exchange resin or the like, followed by crystallization from the solution or column chromatography, to thereby separate and purify the organic acid.

Furthermore, in the present invention, after the production of a non-amino organic acid by the method of the present invention as described above, a polymerization reaction may be carried out using the obtained non-amino organic acid as a raw material to produce a polymer containing the non-amino organic acid. In recent years, the number of environmentally-friendly industrial products has increased, and polymers prepared from raw materials of a plant origin have been attracting attention. The succinic acid produced in the present invention can be processed into polymers such as polyester and polyamide. In addition, the succinic acid obtained by the production method of the present invention or a composition containing succinic acid can be used for food additives, pharmaceutical agents, cosmetics, and the like.

EXAMPLES

Hereinafter, the present invention will be described in further detail with reference to examples. However, the present invention is not limited to these examples.

Example 1

<Construction of a Gene Disruption Vector>

(A) Extraction of *Bacillus subtilis* Genomic DNA

*Bacillus subtilis* ISW1214 was cultured until a late logarithmic growth phase in a 10 mL of LB medium [composition: 10 g of tryptone, 5 g of yeast extract, and 5 g of NaCl dissolved in 1 L of distilled water], and the bacterial cells were collected. The obtained bacterial cells were suspended in 0.15 mL of 10 mM NaCl/20 mM Tris buffer (pH of 8.0)/1 mM EDTA.2Na containing 10 mg/mL of lysozyme.

Then, proteinase K was added to the suspension at a final concentration of 100 μg/mL, and maintained at 37° C. for 1 hour. Then, sodium dodecyl sulfate solution was added thereto at a final concentration of 0.5%, and maintained at 50° C. for 6 hours for lysis. To this lysate, an equal amount of a phenol/chloroform solution was added, and shaken slowly at room temperature for 10 minutes. Then, the total suspension was subjected to centrifugation (5,000×g, 20 minutes, 10 to 12° C.), and a supernatant fraction was taken. Sodium acetate solution was added to the supernatant fraction at a concentration of 0.3 M, and then twice amount of ethanol was added and mixed. A precipitate was recovered by centrifugation (15,000×g, 2 minutes), then washed with 70% ethanol and air dried. 5 mL of 10 mM Tris buffer (pH of 7.5)/1 mM EDTA.2Na was added to the obtained DNA. The resultant solution was left standing overnight at 4° C., and used as a template DNA for PCR.

(B) Amplification and Cloning of SacB Gene by PCR

A *Bacillus subtilis* SacB gene was obtained by performing PCR by using the DNA prepared in the above section (A) as a template; and using synthetic DNAs (SEQ ID NOS: 1 and 2) designed based on the reported nucleotide sequence of the gene (GenBank Database Accession No. X02730).

The composition of the reaction solution is as follows. 1 μL of the template DNA, 0.2 μL of PfxDNA polymerase (available from Invitrogen), 1-fold concentration of the supplied buffer, 0.3 μM of respective primers, 1 mM $MgSO_4$, and 0.25 μM dNTPs were mixed, and total volume of the reaction solution was adjusted to 20 μL.

Reaction temperature condition is as follows: The DNA Thermal Cycler PTC-2000 manufactured by MJ Research Co., Ltd. was used and a cycle of 94° C. for 20 seconds and 68° C. for 2 minutes was repeated 35 times. For the first cycle, heat-retention at 94° C. was conducted for 1 minute 20 seconds. For the last cycle, the heat-retention at 68° C. was conducted for 5 minutes.

An amplified product was analyzed by separating it in 0.75% agarose (SeaKem GTG agarose, available from FMC BioProducts) gel electrophoresis and visualizing with ethidium bromide staining, to thereby detect a fragment of about 2 kb. The target DNA fragment was recovered from the gel by using QIAQuick Gel Extraction Kit (available from QIAGEN).

A 5'-end of the recovered DNA fragment was phosphorylated with T4 Polynucleotide Kinase (available from Takara Shuzo Co., Ltd.) and was inserted into an EcoRV site of the *Escherichia coli* vector (pBluescript II: available from STRATEGENE) by using Ligation Kit ver. 2 (available from Takara Shuzo Co., Ltd.), and the obtained plasmid DNA was used to transform *Escherichia coli* (DH5α strain). The obtained recombinant *Escherichia coli* was spread over an LB agar medium (10 g of tryptone, 5 g of yeast extract, 5 g of NaCl, and 15 g of agar dissolved in 1 L of distilled water) containing 50 μg/mL ampicillin and 50 μg/mL X-Gal.

Clones each forming a white colony on this medium were transferred to an LB agar medium containing 50 μg/mL ampicillin and 10% sucrose, and was cultured at 37° C. for 24 hours. Of those clones, clones which could not grow on the medium containing sucrose were subjected to liquid culture by a conventional method, and then the plasmid DNA was isolated. An *Escherichia coli* strain in which SacB gene is functionally expressed must be incapable of growing in the medium containing sucrose. The obtained plasmid DNA was digested with restriction enzymes SalI and PstI. The plasmid DNA was confirmed to have an insert of about 2 kb and the plasmid was named pBS/SacB.

(C) Construction of Chloramphenicol-Resistant SacB Vector 500 ng of *Escherichia coli* plasmid vector pHSG396 (chloramphenicol resistant marker, available from Takara Shuzo Co., Ltd.) was reacted with 10 units of restriction enzyme PshBI at 37° C. for 1 hour, and recovered by phenol/chloroform extraction and ethanol precipitation. Both ends of the resultant DNA were each made blunt with Klenow Fragment (available from Takara Shuzo Co., Ltd.), and MluI linker (available from Takara Shuzo Co., Ltd.) was ligated thereto by using the Ligation Kit ver. 2 (available from Takara Shuzo Co., Ltd.) to form a circular plasmid, and the obtained plasmid was used to transform the *Escherichia coli* (DH5α strain). The obtained recombinant *Escherichia coli* was spread on an LB agar medium containing 34 μg/mL chloramphenicol. A plasmid DNA was isolated from the obtained clones by a conventional method. A clone having a cleavage site of a restriction enzyme MluI was selected and named pHSG396Mlu.

Meanwhile, pBS/SacB constructed in the above section (B) was digested with the restriction enzymes SalI and PstI, and both ends of the obtained DNA were each made blunt with the Klenow Fragment. The MluI linker was ligated thereto by using the Ligation Kit ver. 2 (available from Takara Shuzo Co., Ltd.). Then, a DNA fragment of about 2.0 kb containing SacB gene was separated in 0.75% agarose gel electrophoresis, and recovered. This SacB gene fragment was ligated to the fragment obtained by digesting pHSG396Mlu with the restriction enzyme MluI and dephosphorylated with Alkaline Phosphatase Calf intestine (available from Takara Shuzo Co., Ltd.), by using the Ligation Kit ver. 2 (available from Takara Shuzo Co., Ltd.), and the obtained DNA was used to transform the *Escherichia coli* (DH5α strain). The obtained recombinant *Escherichia coli* was spread on an LB agar medium containing 34 μg/mL chloramphenicol.

The obtained colonies were transferred to an LB agar medium containing 34 μg/mL chloramphenicol and 10% sucrose, and cultured at 37° C. for 24 hours. Among these clones, plasmid DNA was isolated from the clones which could not grow on the medium containing sucrose by a conventional method. The obtained plasmid DNA was subjected to MluI digestion and analyzed. As a result, the plasmid DNA was confirmed to have an insert of about 2.0 kb and named pCMB 1.

(D) Acquisition of Kanamycin-Resistant Gene

A kanamycin-resistant gene was obtained by performing PCR using a DNA of *Escherichia coli* plasmid vector pHSG299 (kanamycin resistant marker, Takara Shuzo Co., Ltd.) as a template; and using synthetic DNAs (shown in SEQ ID NOS: 3 and 4) as primers. The composition of the reaction solution is as follows: 1 ng of the template DNA, 0.1 μL of Pyrobest DNA polymerase (available from Takara Shuzo Co., Ltd.), 1-fold concentration of the supplied buffer, 0.5 μM of respective primers, and 0.25 μM dNTPs were mixed, and a total volume of the reaction solution was adjusted to 20 μL.

Reaction temperature condition is as follows: The DNA Thermal Cycler PTC-2000 manufactured by MJ Research Co., Ltd. was used and a cycle of 94° C. for 20 seconds, 62° C. for 15 seconds, and 72° C. for 1 minute 20 seconds was repeated 20 times. For the first cycle, heat-retention at 94° C. was conducted for 1 minute 20 seconds. For the last cycle, the heat-retention at 72° C. was conducted for 5 minutes.

An amplified product was analyzed by separating in 0.75% agarose (SeaKem GTG agarose, available from FMC BioProducts) gel electrophoresis and visualizing with ethidium bromide staining, to thereby detect a fragment of about 1.1 kb. The target DNA fragment was recovered from the gel by using the QIAQuick Gel Extraction Kit (available from QIAGEN). A 5'-end of the recovered DNA fragment was phosphorylated with T4 Polynucleotide Kinase (available from Takara Shuzo Co., Ltd.).

(E) Construction of Kanamycin-Resistant SacB Vector

A DNA fragment of about 3.5 kb obtained by digesting pCMB1 constructed in the above section (C) with restriction enzymes Van91I and ScaI was separated in 0.75% agarose gel electrophoresis, and recovered. The resultant DNA was mixed with the kanamycin resistant gene prepared in the above section (D) and ligated thereto by using the Ligation Kit ver. 2 (available from Takara Shuzo Co., Ltd.), and the obtained plasmid DNA was used to transform the *Escherichia coli* (DH5α strain). The obtained recombinant *Escherichia coli* was spread on an LB agar medium containing 50 μg/mL kanamycin.

A strain grown on the medium containing kanamycin was confirmed to be incapable of growing on the medium containing sucrose. Furthermore, the plasmid DNA prepared from the same strain showed the fragments of 354, 473, 1,807, and 1,997 bp by restriction enzyme HindIII digestion. Thus, it was concluded that the plasmid has the structure shown in FIG. 1, and the plasmid was named pKMB 1.

Example 2

Construction of LDH Gene-Disrupted Strain (A) Extraction of a Genomic DNA from *Brevibacterium flavum* MJ233-ES Strain The *Brevibacterium flavum* MJ-233 strain was cultured until the late stage of logarithmic growth phase in a 10 mL A medium (2 g of urea, 7 g of $(NH_4)_2SO_4$, 0.5 g of $KH_2PO_4$, 0.5 g of $K_2HPO_4$, 0.5 g of $MgSO_4.7H_2O$, 6 mg of $FeSO_4.7H_2O$, 6 mg of $MnSO_4.4\text{-}5H_2O$, 200 μg of biotin, 100 μg of thiamine, 1 g of yeast extract, 1 g of casamino aid, and 20 g of glucose dissolved in 1 L of distilled water). The obtained bacterial cells were used to prepare a genomic DNA by the method described in the above section (A) of Example 1.

(B) Cloning of a Lactate Dehydrogenase Gene

A lactate dehydrogenase gene of MJ233 strain was obtained by performing PCR by: using the DNA prepared in the above section (A) as a template; and using synthetic DNAs (SEQ ID NOS: 5 and 6) designed based on the nucleotide sequence of the gene described in JP11-206385A. The composition of the reaction solution is as follows: 1 μL of the template DNA, 0.2 μL of TaqDNA polymerase (available from Takara Shuzo Co., Ltd.), 1 time concentration of a supplied buffer, 0.2 μM of respective primers, and 0.25 μM dNTPs were mixed, and a total volume of the reaction liquid was adjusted to 20 μL.

Reaction temperature condition is as follows: The DNA Thermal Cycler PTC-2000 manufactured by MJ Research Co., Ltd. was used and a cycle of 94° C. for 20 seconds, 55° C. for 20 seconds, and 72° C. for 1 minute was repeated 30 times. For the first cycle, heat-retention at 94° C. was conducted for 1 minute 20 seconds. For the last cycle, the heat-retention at 72° C. was conducted for 5 minutes.

The amplified product was analyzed by separating in 0.75% agarose (SeaKem GTG agarose, available from FMC BioProducts) gel electrophoresis and visualizing with ethidium bromide staining, to thereby detect a fragment of about 0.95 kb. The target DNA fragment was recovered from the gel by using QIAQuick Gel Extraction Kit (available from QIAGEN).

The recovered DNA fragment was mixed with the PCR product-cloning vector pGEM-T Easy (available from Promega Corporation) and ligated thereto using Ligation Kit ver. 2 (available from Takara Shuzo Co., Ltd.), and the obtained plasmid DNA was used to transform *Escherichia coli* (DH5α strain). The obtained recombinant *Escherichia coli* was spread on an LB agar medium containing 50 μg/mL ampicillin and 50 μg/mL X-Gal.

Clones each forming a white colony on this medium were subjected to liquid culture by a conventional method, and then the plasmid DNA was purified. The obtained plasmid DNA was cleaved with restriction enzymes SacI and SphI. The plasmid DNA was confirmed to have an insert of about 1.0 kb and named pGEMT/CgLDH.

(C) Construction of a Plasmid for Disrupting Lactate Dehydrogenase Gene pGEMT/CgLDH prepared in the above section (B) was digested with restriction enzymes EcoRV and XbaI to remove a coding region of lactate dehydrogenase of about 0.25 kb. The each end of the remaining DNA fragment of about 3.7 kb was made blunt by the Klenow Fragment and self-ligated by using the Ligation Kit ver. 2 (available from Takara Shuzo Co., Ltd.), and the obtained plasmid was used to transform the *Escherichia coli* (DH5α strain). The obtained recombinant *Escherichia coli* was spread on an LB agar medium containing 50 μg/mL ampicillin.

A strain grown on this medium was subjected to liquid culture by a conventional method, and then the plasmid DNA was isolated. The obtained plasmid DNA was digested with restriction enzymes SacI and SphI. A clone having an insert of about 0.75 kb was selected and named pGEMT/ΔLDH.

Next, the DNA fragment of about 0.75 kb obtained by digesting pGEMT/ΔLDH with the restriction enzymes SacI and SphI was separated in 0.75% agarose gel electrophoresis and recovered, to prepare a lactate dehydrogenase gene fragment in which a part of its region is deleted. This DNA fragment was mixed with the pKMB1 constructed in Example 1 digested with the restriction enzymes SacI and SphI, and ligated thereto by using the Ligation Kit ver. 2 (available from Takara Shuzo Co., Ltd.), and the obtained plasmid DNA was used to transform the *Escherichia coli* (DH5α strain). The obtained recombinant *Escherichia coli* was spread on an LB agar medium containing 50 μg/mL kanamycin and 50 μg/mL X-Gal.

Figure 2:
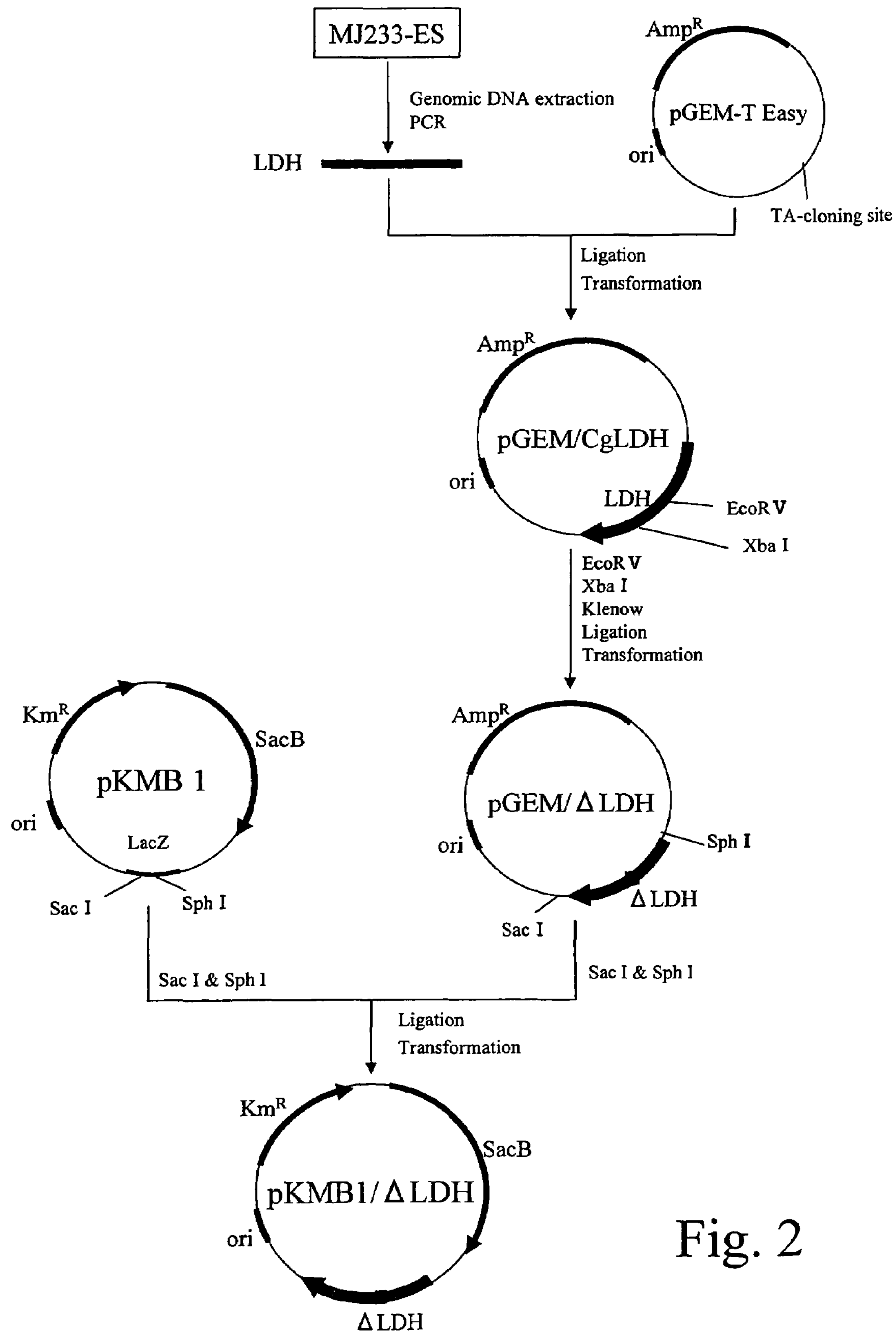
FIG. 2 shows a procedure for constructing the plasmid pKMB1/ΔLDH.

Clones each forming a white colony on this medium was subjected to liquid culture by a conventional method, and then the plasmid DNA was isolated. The obtained plasmid DNA was digested with restriction enzymes SacI and SphI. A clone having an insert of about 0.75 kb was selected and named pKMB1/ΔLDH (FIG. 2).

(D) Construction of Lactate Dehydrogenase Gene-Disrupted Strain Derived from *Brevibacterium flavum* MJ233-ES Strain A plasmid DNA to be used for transformation of the *Brevibacterium flavum* MJ-233 strain was isolated from *Escherichia coli* JM110 strain transformed with pKMB1/ΔLDH by a calcium chloride method (Journal of Molecular Biology, 53, 159, 1970).

Endogenous plasmids were removed from *Brevibacterium flavum* MJ233 strain (FERM BP-1497) (curing) according to the conventional procedures (Wolf H et al., J. Bacteriol. 1983, 156 (3) 1165-1170, Kurusu Y et al., Agric Biol. Chem. 1990, 54(2) 443-7) and then, the resulting plasmid-cured strain *Brevibacterium flavum* MJ233-ES was used for subsequent transformation.

The transformation of the *Brevibacterium flavum* MJ233-ES strain was performed by an electric pulse method (Res. Microbiolo., Vol. 144, p. 181-185, 1993), and the obtained transformant was spread on an LBG agar medium (10 g of tryptone, 5 g of yeast extract, 5 g of NaCl, 20 g of glucose, and 15 g of agar dissolved in 1 L of distilled water) containing 50 μg/mL kanamycin.

Because pKMB 1/ΔLDH is a plasmid incapable of replicating in the *Brevibacterium flavum* MJ233-ES strain, a strain grown on this medium must have a kanamycin-resistant gene and SacB gene derived from the plasmid on its genome, as a result of homologous recombination between a lactate dehydrogenase gene on the plasmid and the same gene on the genome of the *Brevibacterium flavum* MJ-233 strain.

Next, the strain obtained by homologous recombination was subjected to liquid culture on an LBG medium containing 50 μg/mL kanamycin. The culture solution supposed to contain about 1,000,000 bacterial cells was spread on an LBG medium containing 10% sucrose. As a result, about 10 sucrose-insensitive strains in which the SacB gene was removed by the second homologous recombination were obtained.

The obtained strains include: a strain in which the lactate dehydrogenase gene was replaced by a deletion type derived from pKMB1/ΔLDH; and a strain in which the lactate dehydrogenase gene reverted to a wild type. Whether the lactate dehydrogenase gene is a deletion type or a wild type can be confirmed easily by subjecting a bacterial strain obtained by liquid culture in an LBG medium to direct PCR and detecting the lactate dehydrogenase gene. Analysis of the lactate dehydrogenase gene by using primers (SEQ ID NOS: 7 and 8) for PCR amplification results in a DNA fragment of 720 bp for a wild type and a DNA fragment of 471 bp for a deletion type.

As a result of the analysis of the sucrose-insensitive strain by the above-mentioned method, a strain having only a deletion type gene was selected and named *Brevibacterium flavum* MJ233/ΔLDH.

(E) Measurement of Lactate Dehydrogenase Activity

*Brevibacterium flavum* MJ233/ΔLDH strain prepared by the above (D) was inoculated into the culture medium A and then aerobically cultured at 30° C. for 15 hour with shaking. The resulting culture was centrifuged (3,000×g, 4° C. for 20 minutes) and bacterial cells were then collected, followed by washing with sodium-phosphate buffer (50 mM sodium phosphate buffer (pH 7.3)).

Subsequently, 0.5 g (wet weight) of washed bacterial cells was suspended in 2 ml of the above sodium-phosphate buffer and then treated with ultrasonicator (manufactured by Branson, Ltd.) on ice to obtain a lysis product of bacterial cells. The lysis product was centrifuged (10,000×g, 4° C. for 30 minutes) and the supernatant was then obtained as a crude enzyme solution. Similarly, a crude enzyme solution of *Brevibacterium flavum* MJ233-ES strain was prepared as a control and then subjected to the following activity measurement.

The lactate dehydrogenase activity was measured by determining the oxidation of coenzyme NADH to $NAD^+$ as a change in absorbance at 340 nm in connection with the generation of lactic acid from pyruvic acid as a substrate (L. Kanarek and R. L. Hill, J. Biol. Chem. 239, 4202 (1964)). The reaction was carried out at 37° C. in 50 mM potassium-phosphate buffer (pH 7.2) in the presence of 10 mM pyruvic acid and 0.4 mM NADH. Consequently, the lactate dehydrogenase activity of the crude enzyme solution prepared from *Brevibacterium flavum* MJ233/ΔLDH strain was one tenth or less of the lactate dehydrogenase activity of the crude enzyme solution prepared from *Brevibacterium flavum* MJ233-ES strain.

Example 3

Construction of Expression Vector for Coryneform Bacterium (A) Preparation of a Promoter Fragment for Coryneform Bacterium A DNA fragment (hereinafter, referred to TZ4 promoter) shown in SEQ ID NO: 4 in JP07-95891A and reported to have high promoter activity in a coryneform bacterium was used. The promoter fragment was obtained by performing PCR by using the *Brevibacterium flavum* MJ233 genomic DNA prepared in the section (A) of Example 2 as a template; and using synthetic DNAs (SEQ ID NOS: 9 and 10) designed based on a sequence described as SEQ ID NO: 4 in JP07-95891A, as primers.

The composition of the reaction solution is as follows: 1 μL of the template DNA, 0.2 μL of PfxDNA polymerase (available from Invitrogen Japan K.K.), 1 time concentration of a supplied buffer, 0.3 μM of respective primers, 1 mM $MgSO_4$, and 0.25 μM dNTPs were mixed, and a total volume of the reaction solution was adjusted to 20 μL.

Reaction temperature condition is as follows: The DNA Thermal Cycler PTC-2000 manufactured by MJ Research Co., Ltd. was used and a cycle of 94° C. for 20 seconds, 60° C. for 20 seconds, and 72° C. for 30 seconds was repeated 35 times. For the first cycle, heat-retention at 94° C. was conducted for 1 minute 20 seconds. For the last cycle, the heat-retention at 72° C. was conducted for 2 minutes.

The amplified product was analyzed by separating in 2.0% agarose (SeaKem GTG agarose, available from FMC Bio-Products) gel electrophoresis and visualizing with ethidium bromide staining, to thereby detect a fragment of about 0.25 kb. The target DNA fragment was recovered from the gel by using the QIAQuick Gel Extraction Kit (available from QIAGEN).

The 5'-end of the recovered DNA fragment was phosphorylated with T4 Polynucleotide Kinase (available from Takara Shuzo Co., Ltd.) and was ligated to an SmaI site of an *Escherichia coli* vector pUC19 (Takara Shuzo Co., Ltd.) by using the Ligation Kit ver. 2 (available from Takara Shuzo Co., Ltd.), and the obtained plasmid DNA was used to transform the *Escherichia coli* (DH5α strain). The obtained recombinant *Escherichia coli* was spread on an LB agar medium containing 50 μg/mL ampicillin and 50 μg/mL X-Gal.

Six clones each forming a white colony on this medium were subjected to liquid culture by a conventional method, and then the plasmid DNA was isolated, and the nucleotide sequence was determined. Of those, a clone having a TZ4 promoter inserted therein so to have transcription activity in an opposite direction with respect to the lac promoter on pUC 19 was selected and named pUC/TZ4.

Next, a DNA linker consisting of synthetic DNAs (SEQ ID NOS: 11 and 12) each having phosphorylated 5'-ends and having sticky ends corresponding to each of BamHI and PstI was added to the DNA fragment prepared by digesting pUC/TZ4 with restriction enzymes BamHI and PstI, and ligated with each other by using the Ligation Kit ver. 2 (available from Takara Shuzo Co., Ltd.), and the obtained plasmid DNA was used to transform the *Escherichia coli* (DH5α strain). This DNA linker includes a ribosome binding sequence (AGGAGG) and a cloning site (the order of PacI, NotI, and ApaI from upstream) arranged downstream of the ribosome binding sequence.

Clones each forming a white colony on this medium were subjected to liquid culture by a conventional method, and then the plasmid DNA was isolated. Of the obtained plasmid DNAs, a plasmid DNA capable of being cleaved with a restriction enzyme NotI was selected and named pUC/TZ4-SD.

A promoter fragment of about 0.3 kb was obtained by digesting the pUC/TZ4-SD with a restriction enzyme PstI, making its end blunt with the Klenow Fragment, and cleaving the resultant DNA with a restriction enzyme KpnI, and separated in 2.0% agarose gel electrophoresis, and recovered.

(B) Construction of Expression Vector for Coryneform Bacterium pHSG298par-rep described in JP 12-93183A was used as a plasmid capable of stable and autonomous replication in coryneform bacteria. This plasmid includes a replicating region and a region having a stabilization function of a natural plasmid pBY503 from *Brevibacterium stationis* IFO12144 strain, a kanamycin resistant gene derived from an *Escherichia coli* vector pHSG298 (Takara Shuzo Co., Ltd.), and a replicating region for *Escherichia coli*.

A DNA was prepared by digesting pHSG298par-rep with a restriction enzyme SseI, making its end blunt with the Klenow Fragment, and digesting the resultant DNA with the restriction enzyme KpnI, and the DNA was mixed with the TZ4 promoter fragment prepared in the above section (A) and ligated thereto by using the Ligation Kit ver. 2 (available from Takara Shuzo Co., Ltd.), and the the obtained plasmid DNA was used to transform the *Escherichia coli* (DH5α strain). The obtained recombinant *Escherichia coli* was spread on an LB agar medium containing 50 μg/mL kanamycin.

Figure 3:
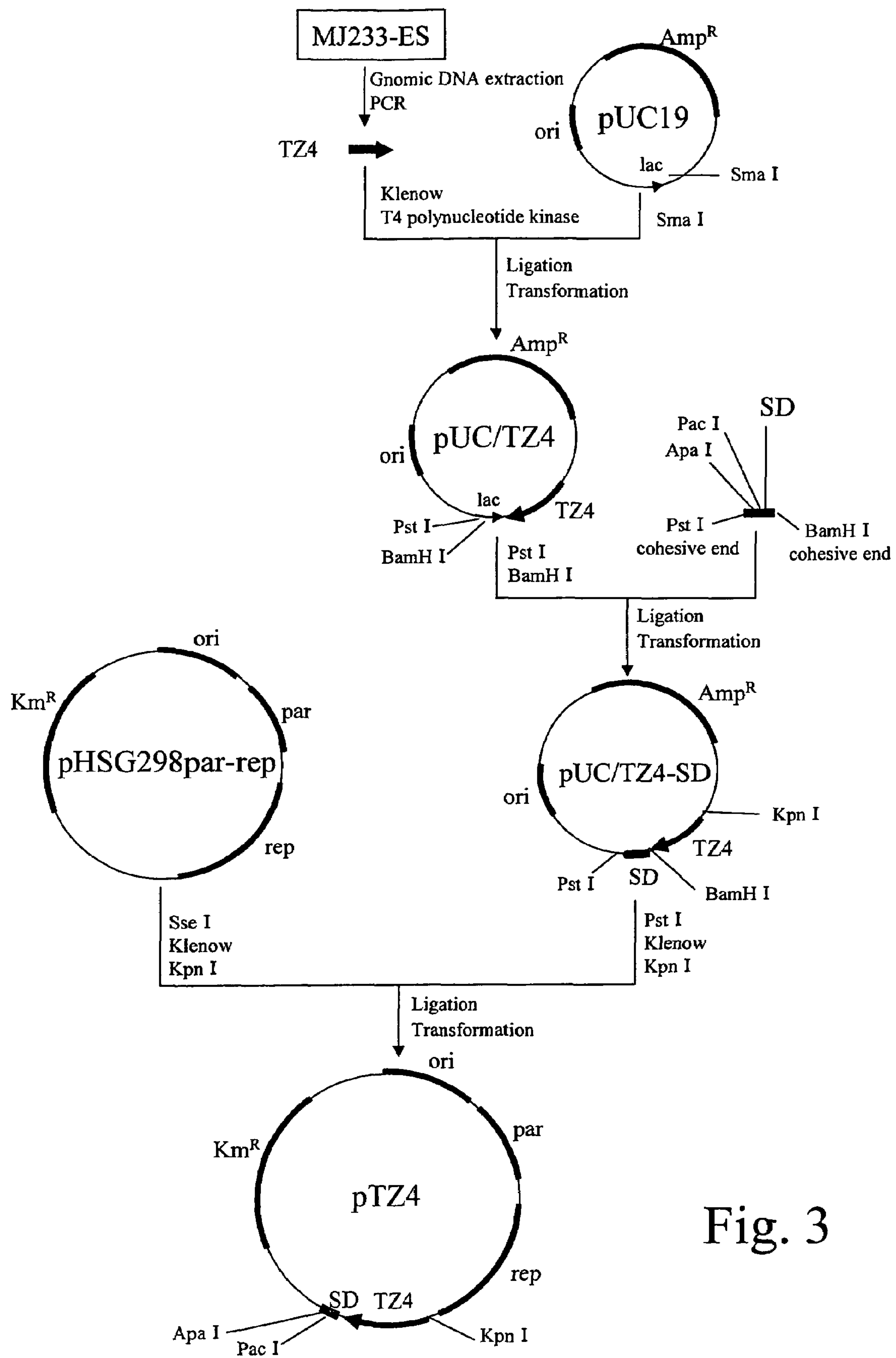
FIG. 3 shows a procedure for constructing the plasmid pTZ4.

A strain grown on this medium was subjected to liquid culture by a conventional method, and then the plasmid DNA was purified. Of the obtained plasmid DNA, a plasmid DNA capable of being digested with the restriction enzyme NotI was selected and named pTZ4 (FIG. 3 shows the construction procedure).

Example 4

Construction of Pyruvate Carboxylase Activity-Enhanced Strain (A) Acquisition of a Pyruvate Carboxylase Gene A pyruvate carboxylase gene derived from the *Brevibacterium flavum* MJ233 strain was obtained by performing PCR by using the DNA prepared in the section (A) of Example 2 as a template; and using synthetic DNAs (SEQ ID NOS: 13 and 14) designed based on a sequence of a pyruvate carboxylase gene of a *Corynebacterium glutamicum* ATCC 13032 strain whose entire genomic sequence was reported (GenBank Database Accession No. AP005276).

The composition of the reaction solution is as follows: 1 μL of the template DNA, 0.2 μL of PfxDNA polymerase (available from Invitrogen Japan K.K.), 1-fold concentration of the supplied buffer, 0.3 μM of respective primers, 1 mM $MgSO_4$, and 0.25 μM dNTPs were mixed, and a total volume of the reaction liquid was adjusted to 20 μL.

Reaction temperature condition is as follows: The DNA Thermal Cycler PTC-2000 manufactured by MJ Research Co., Ltd. was used and a cycle of 94° C. for 20 seconds and 68° C. for 4 minutes was repeated 35 times. For the first cycle, heat-retention at 94° C. was conducted for 1 minute 20 seconds. For the last cycle, the heat-retention at 68° C. was conducted for 10 minutes. After completion of PCR, 0.1 M of Takara Ex Taq (Takara Shuzo Co., Ltd.) was added and kept at 72° C. for 30 minutes.

The amplified product was analyzed by separating in 0.75% agarose (SeaKem GTG agarose, available from FMC BioProducts) gel electrophoresis and visualizing with ethidium bromide staining, to thereby detect a fragment of about 3.7 kb. The target DNA fragment was recovered from the gel by using the QIAQuick Gel Extraction Kit (available from QIAGEN).

The recovered DNA fragment was mixed with the PCR product-cloning vector pGEM-TEasy (available from Promega Corporation) and ligated thereto by using the Ligation Kit ver. 2 (available from Takara Shuzo Co., Ltd.), and the obtained plasmid DNA was used to transform *Escherichia coli* (DH5α strain). The obtained recombinant *Escherichia coli* was spread on an LB agar medium containing 50 μg/mL ampicillin and 50 μg/mL X-Gal.

Clones each forming a white colony on this medium were subjected to liquid culture by a conventional method, and then the plasmid DNA was isolated. The obtained plasmid DNA was digested with restriction enzymes PacI and ApaI. The plasmid DNA was confirmed to have an insert of about 3.7 kb and named pGEM/MJPC.

A nucleotide sequence of the insert in pGEM/MJPC was determined by using the nucleotide sequencing device (model 377 XL, manufactured by Applied Biosystems) and BigDye Terminator Cycle Sequencing Kit ver. 3 (manufactured by Applied Biosystems). SEQ ID NO: 15 shows the determined nucleotide sequence and a predicted amino acid sequence. The amino acid sequence is extremely highly homologous (99.4%) to that derived from the *Corynebacterium glutamicum* ATCC13032 strain, concluding that the pGEM/MJPC insert was a pyruvate carboxylase gene derived from the *Brevibacterium flavum* MJ233 strain.

(B) Construction of Plasmid for Enhancing Pyruvate Carboxylase Activity

Next, the pyruvate carboxylase gene fragment of about 3.7 kb obtained by digesting pGEM/MJPC with the restriction enzymes PacI and ApaI in the above section (A) was separated in 0.75% agarose gel electrophoresis, and recovered.

This DNA fragment was mixed with pTZ4 digested with the restriction enzymes PacI and ApaI in Example 3 and ligated thereto by using the Ligation Kit ver. 2 (available from Takara Shuzo Co., Ltd.), and the obtained plasmid DNA was used to transform the *Escherichia coli* (DH5α strain). The obtained recombinant *Escherichia coli* was spread on an LB agar medium containing 50 μg/mL kanamycin.

Figure 4:
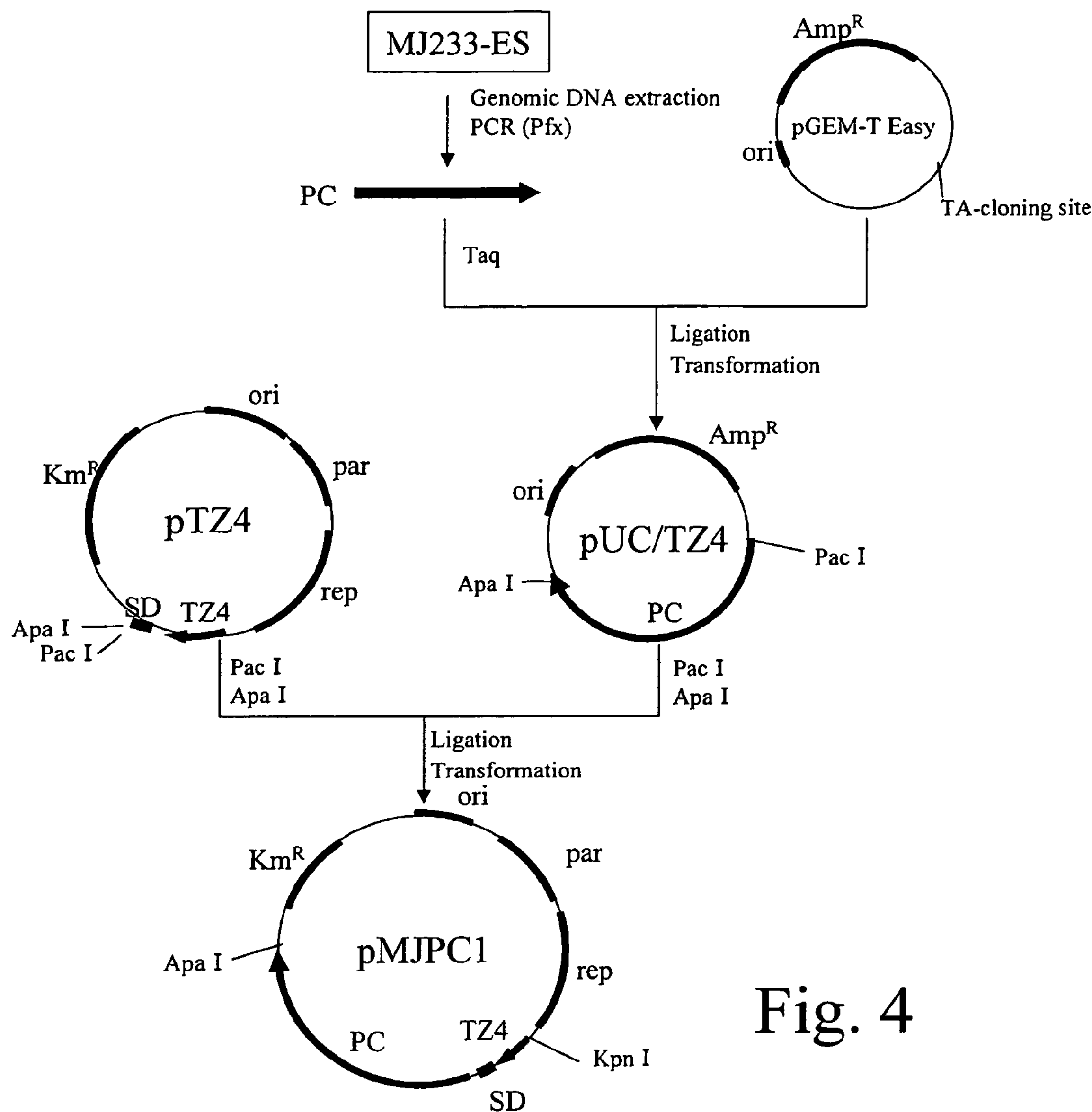
FIG. 4 shows a procedure for constructing the plasmid pMJPC1.

Strains grown on this medium were subjected to liquid culture by a conventional method, and then the plasmid DNA was purified. The obtained plasmid DNA was digested with restriction enzymes PacI and ApaI. A clone having an insert of about 3.7 kb was selected and named pMJPC1 (FIG. 4).

(C) Transformation of *Brevibacterium flavum* MJ233/ΔLDH Strain

A plasmid DNA pMJPC 1 which is capable of replicating in the *Brevibacterium flavum* MJ233 strain was isolated from the *Escherichia coli* (DH5α strain) transformed in the above section (B).

The transformation of the *Brevibacterium flavum* MJ233/ΔLDH strain was performed by the electric pulse method (Res. Microbiolo., Vol. 144, p. 181-185, 1993), and the obtained transformant was spread on an LBG agar medium (10 g of tryptone, 5 g of yeast extract, 5 g of NaCl, 20 g of glucose, and 15 g of agar dissolved in 1 L of distilled water) containing 50 μg/mL kanamycin.

A strain grown on this medium was subjected to liquid culture by a conventional method, and then the plasmid DNA was extracted and analyzed with restriction enzyme digestion. The results confirmed that the strain retained pMJPC 1, and the strain was named *Brevibacterium flavum* MJ233/PC/ΔLDH strain.

(D) Pyruvate Carboxylase Activity

The transformant strain *Brevibacterium flavum* MJ233/PC/ΔLDH obtained in the above section (C) was cultured overnight in 100 ml of the culture medium A containing 2% glucose and 25 mg/l kanamycin. The obtained bacterial cells were harvested and then washed with 50 ml of 50 mM potassium phosphate buffer (pH 7.5), followed by re-suspension in 20 ml of buffer having the same composition as mentioned above. The suspension was subjected to sonication with SONIFIER 350 (manufactured by Branson) and the centrifuged supernatant was then provided as cell-free extracts. The pyruvate carboxylase activity was determined using the resulting cell-free extracts. The measurement of enzyme activity was carried out by allowing the enzyme to react at 25° C. in a reaction solution containing 100 mM Tris/HCl buffer (pH 7.5), 0.1 mg/10 ml biotin, 5 mM magnesium chloride, 50 mM sodium hydrogen carbonate, 50 mM sodium pyruvate, 5 mM adenosine triphosphate disodium, 0.32 mM NADH, 20 units/1.5 ml malate dehydrogenase (manufactured by WAKO, originated from yeast). One unit (1 U) was defined as the amount of enzyme for catalyzing a decrease of 1 μmol of NADH per minute. The specific activity in the cell-free extracts of the strain transformed with pyruvate carboxylase gene was 0.2 U/mg of protein. On the other hand, from the bacterial cells prepared by similarly incubating the parent MJ233/ΔLDH strain using the culture medium A, no pyruvate carboxylase activity was detected by the activity measurement method.

Example 5

Cloning of *Escherichia coli* Fumarate Reductase Gene (A) Extraction of *Escherichia coli* DNA

*Escherichia coli* JM109 strain was incubated in 10 ml of LB culture medium until the late stage of the logarithmic growth phase, and the resulting bacterial cells were then subjected to the method described in the section (A) of Example 1 to prepare a genomic DNA.

(B) Cloning of *Escherichia coli* Fumarate Reductase Gene

The *Escherichia coli* fumarate reductase gene was obtained by PCR using the DNA prepared in the above section (A) as a template and synthetic DNAs (SEQ ID NOS: 17 and 18) designed on the basis of the sequence of the gene of *Escherichia coli* K12-MG1655 strain whose the whole genome sequence had been reported (GenBank Database Accession NO. U00096).

Composition of reaction solution is as follows: 1 μL of template DNA, 0.2 μL of PfxDNA polymerase (manufactured by Invitrogen Co., Ltd.), 1-fold concentration of the supplied buffer, 0.3 μM of respective primers, 1 mM $MgSO_4$, and 0.25 μM of dNTPs were mixed, and the total volume was adjusted to 20 μL.

Reaction temperature condition is as follows: The DNA Thermal Cycler PTC-2000 manufactured by MJ Research Co., Ltd. was used and a cycle of 94° C. for 20 seconds and 68° C. for 4 minutes was repeated 35 times. For the first cycle, heat-retention at 94° C. was conducted for 1 minute 20 seconds. For the last cycle, the heat-retention at 68° C. was conducted for 10 minutes. After completion of PCR, 0.1 L of Takara Ex Taq (Takara Shuzo Co., Ltd.) was added and kept at 72° C. for 30 minutes.

The amplified product was analyzed by separating in 0.75% agarose (Sea Kem GTG agarose: manufactured by FMC BioProducts) gel electrophoresis and then visualized with ethidium bromide staining, thereby detecting a fragment of about 3.8 kb. The DNA fragment of interest was isolated from the gel by means of QIA Quick Gel Extraction Kit (manufactured by QIAGEN).

The recovered DNA fragment was mixed with the PCR product-cloning vector pT7 Blue T-Vector (manufactured by Novagen) and ligated thereto by Ligation Kit ver. 2 (manufactured by Takara Shuzo Co., Ltd.), and the obtained plasmid DNA was used to transform *Escherichia coli* (DH5α strain). The obtained recombinant *Escherichia coli* was spread on an LB agar culture medium containing 50 μg/mL ampicillin and 50 μg/mL X-Gal.

A clone forming a white colony on the culture medium was incubated in liquid culture according to a conventional method, followed by purifying the plasmid DNA. The resulting plasmid DNA was digested with restriction enzymes HindIII and KpnI, thereby confirming an insert fragment of about 3.9 kb, and named pFRD6.0.

The nucleotide sequence of the insert fragment of pFRD6.0 was determined using the nucleotide sequencing device (model 377XL) manufactured by Applied Biosystems, Inc. and BigDye Terminator Cycle Sequencing Kit ver. 3. The resulting nucleotide sequences and predicted amino acid sequences are described in SEQ ID NOS: 19 and 20-23.

Example 6

Construction of a Strain with Enhanced Activities of Pyruvate Carboxylase/Fumarate Reductase (A) Modification of a Restriction Enzyme Recognition Site of pMJPC1 pMJPC1 constructed in Example 3 was completely digested with the restriction enzyme KpnI, and its 5'-ends was dephosphorylated by a reaction with Calf intestine Alkaline Phosphatase (Takara Shuzo Co., Ltd.). The DNA linker consisting of the synthetic DNAs with phosphorylated 5'-ends (SEQ ID NOS: 24 and 25) was mixed with the obtained fragment and ligated thereto using the Ligation Kit ver. 2 (available from Takara Shuzo Co., Ltd.), and the obtained plasmid DNA was used to transform the *Escherichia coli* (DH5α strain). The obtained recombinant *Escherichia coli* was spread on an LB agar medium containing 50 μg/mL kanamycin.

A strain grown on this medium was subjected to liquid culture by a conventional method, and then the plasmid DNA was isolated. Of the obtained plasmid DNA, a plasmid DNA which can be digested with the restriction enzyme NdeI was selected and named pMJPC1.1.

(B) Construction of a Plasmid for Enhancing Activities of Pyruvate Carboxylase and Fumarate Reductase A DNA fragment of about 3.9 kb was obtained by digesting pFRD6.0 prepared in Example 5 with the restriction enzyme HindIII, and making its end blunt with the Klenow Fragment, and digesting with the restriction enzyme KpnI. The DNA fragment was separated in 0.75% agarose gel electrophoresis, and recovered. The prepared fragment containing the *Escherichia coli* fumarate reductase gene was mixed and ligated, by using the Ligation Kit ver. 2 (available from Takara Shuzo Co., Ltd.), to the DNA which was obtained by digesting pMJPC1.1 prepared in the above section (A) with the restriction enzyme NdeI, making its end blunt with the Klenow Fragment, followed by digestion with the restriction enzyme KpnI. The obtained plasmid DNA was used to transform *Escherichia coli* (DH5α strain). The obtained recombinant *Escherichia coli* was spread on an LB agar medium containing 50 μg/mL kanamycin.

Figure 5:
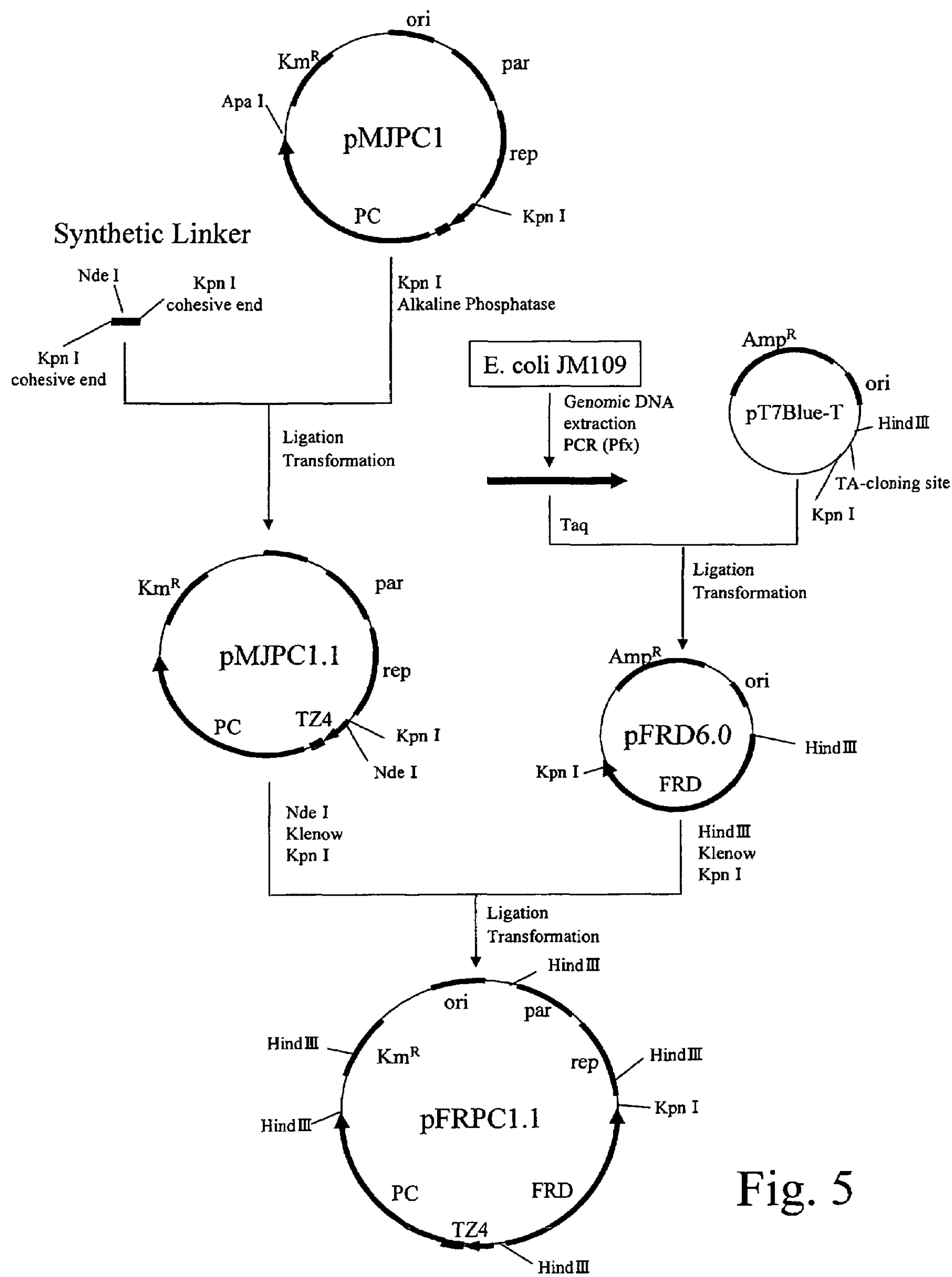
FIG. 5 shows a procedure for constructing the plasmid pFRPC1.1.

A strain grown on this medium was subjected to liquid culture by a conventional method, and then the plasmid DNA was isolated. The obtained plasmid DNA showed fragments of 505, 2,132, 2,675, 3,775, and 4,193 bp after restriction enzyme HindIII digestion. Thus, it was concluded that the DNA has the structure shown in FIG. 5, and the plasmid was named pFRPC 1.1.

(B) Transformation of *Brevibacterium flavum* MJ233/ΔLDH Strain

The transformation of the *Brevibacterium flavum* MJ233/ΔLDH strain with pFRPC1.1 was performed by the method described in the section (C) of Example 4, to thereby obtain a strain having the plasmid pFRPC1.1. This strain was named *Brevibacterium flavum* MJ233/FRD/PC/ΔLDH strain.

(C) FRD Enzyme Activity Measurement

The transformant, *Brevibacterium flavum* MJ233/FRD/PC/ΔLDH strain, prepared by the above section (B) was cultured overnight in 100 ml of the culture medium A containing 2% glucose and 25 mg/L kanamycin. The resulting bacterial cells were collected and washed with 50 ml of 50 mM potassium phosphate buffer (pH 7.5), followed by re-suspension in 20 ml of buffer having the same composition as mentioned above. The suspension was subjected to sonication with SONIFIER 350 (manufactured by Branson) and the centrifuged supernatant was used as cell-free extracts. The fumarate reductase activity was determined using the cell-free extracts. The measurement of enzyme activity was carried out by allowing the extracts to react at 25° C. in a reaction solution containing 33 mM Tris/HCl buffer (pH 7.5), 0.1 mM EDTA, 20 mM sodium succinate, 2 mM $K_3Fe(CN)_6$. One unit (1 U) was defined as the amount of the enzyme for catalyzing a decrease of 2 μmol of $K_3Fe(CN)_6$ per minute. The specific fumarate reductase activity in the cell-free extracts of the strain expressing the plasmid pFRRC1.1 was 0.02 U/mg-protein. On the other hand, in the bacterial cells prepared by similarly culturing the parent MJ233/ΔLDH strain in the culture medium A, the specific activity was 0.01 U/mg-protein.

Example 7

<Reaction While Neutralizing a Medium with Magnesium Carbonate>

100 mL of a medium, which has a composition of 4 g of urea, 14 g of ammonium sulfate, 0.5 g of monobasic potassium phosphate, 0.5 g of dibasic potassium phosphate, 0.5 g of magnesium sulfate heptahydrate, 20 mg of ferrous sulfate heptahydrate, 20 mg of manganese sulfate-hydrate, 200 μg of D-biotin, 200 μg of thiamin hydrochloride, 1 g of yeast extract, 1 g of casamino acid, and 1000 mL of distilled water, was poured into a 500-mL conical flask and then sterilized by heat at 120° C. for 20 minutes. The solution was cooled to room temperature and then added with 4 mL of 50% aqueous glucose solution, which had been previously sterilized, and with 50 μL of 5% aqueous kanamycin solution, which had been sterilized by filtration, followed by inoculation of *Brevibacterium flavum* MJ233/FRD/PC/ΔLDH prepared in Example 6 to carry out seed culture at 30° C. for 24 hours.

A medium containing 12 g of urea, 42 g of ammonium sulfate, 1.5 g of monobasic potassium phosphate, 1.5 g of dibasic potassium phosphate, 1.5 g of magnesium sulfate heptahydrate, 60 mg of ferrous sulfate heptahydrate, 60 mg of manganese sulfate-hydrate, 600 μg of D-biotin, 600 μg of thiamin hydrochloride, 3 g of yeast extract, 3 g of casamino acid, 1 mL of antifoam (Adecanol LG294: manufactured by Asahi Denka Kogyo K.K.), dissolved in 2,500 mL of distilled water was poured into a 5-L fermenter, and then sterilized by heat at 120° C. for 20 minutes. The medium was cooled to room temperature and then added with 500 mL of 12% aqueous glucose solution, which had been previously sterilized, and the whole amount of the seed culture was added thereto, followed by incubation at 30° C. The culture was carried out with aeration at a rate of 500 mL per minute and agitation at a rate of 500 rpm. After 12 hours, the glucose was almost completely consumed.

A medium containing 0.2 g of magnesium sulfate heptahydrate, 8 mg of ferrous sulfate heptahydrate, 8 mg of manganese sulfate-hydrate, 80 μg of D-biotin, 80 μg of thiamin hydrochloride, dissolved in 200 mL of distilled water was poured into a 500-mL conical flask and then sterilized by heat at 120° C. for 20 minutes. After the medium had been cooled to room temperature, it was added to the bacterial cells collected from the culture obtained as described above by centrifugation at 8,000 rpm for 5 minutes, to re-suspend the cells so that O.D. (660 nm) becomes 60. 25 mL of the suspended solution and 25 mL of a previously-sterilized 24% aqueous glucose solution were added to 100-mL conical flask, and 4.215 g of $4MgCO_3.Mg(OH)_2.5H_2O$ was added thereto, followed by mixing. The reaction suspension was maintained at 30° C., and a reaction was carried out with agitation at a rate of 120 rpm. The average sugar consumption rate, succinic acid production rate, and yield thereof over 20 hours from the beginning of the reaction were 2.08 g/L/h, 0.61 g/L/h, and 77%, respectively. The rates of sugar consumption and succinic acid production were represented by an average value from the beginning to the end of the reaction.

Example 8

<Reaction While Neutralizing a Medium with Magnesium Hydroxide (Part 1)>

A medium containing 0.2 g of magnesium sulfate heptahydrate, 8 mg of ferrous sulfate heptahydrate, 8 mg of manganese sulfate-hydrate, 80 μg of D-biotin, 80 μg of thiamin hydrochloride, 1 mL of antifoam (Adecanol LG294: manufactured by Asahi Denka Kogyo K.K.), dissolved in 200 mL of water was poured into a 500-mL conical flask and then sterilized by heat at 120° C. for 20 minutes. After the medium had been cooled to room temperature, it was added to the bacterial cells collected from the culture obtained by a similar method as in Example 7 by centrifugation at 8,000 rpm for 5 minutes to re-suspend the cells so that O.D. (660 nm) becomes 200. 200 mL of the suspension and 200 mL of a previously-sterilized 30% aqueous glucose solution were added in a 1-litter jar fermenter, and then kept at 35° C. The reaction was performed with agitation at 400 rpm and aeration at a rate of 100 mL per minute while maintaining the pH at 6.8 by intermittently adding 4 M aqueous solution of magnesium hydroxide. The average sugar consumption rate, succinic acid production rate, and yield thereof over 46 hours from the beginning of the reaction were 3.22 g/L/h, 1.38 g/L/h, and 72%, respectively.

A reaction suspension was prepared in the same way as described above and maintained at 35° C. The reaction was performed with agitation at 200 rpm and without aeration while maintaining the pH at 6.8 by intermittently adding 4 M magnesium aqueous solution of hydroxide. The average sugar consumption rate, succinic acid production rate, and yield thereof over 50 hours from the beginning of the reaction were 2.06 g/L/h, 0.90 g/L/h, and 55%, respectively.

Example 9

<Reaction While Neutralizing a Medium with Magnesium Hydroxide (Part 2) (Jar Fermenter)>

(A) Preparation of Bacterial Cells

Using the *Brevibacterium flavum* MJ233/PC/ΔLDH strain prepared in Example 4, seed culture was performed in the same way as in Example 7.

150 L of a medium, which contains 100 g of glucose, 0.5 g of magnesium sulfate heptahydrate, 0.65 g of orthophosphoric acid, 14.3 mL of soybean protein hydrolate solution (total nitrogen content 35 g/L), 1.0 g of ammonium sulfate, 20 mg of ferrous sulfate heptahydrate, 20 mg of manganese sulfate hydrate, 1 mg of D-biotin, 1 mg of thiamine hydrochloride, and 0.05 mL of antifoam (GD-113: manufactured by NOF Corporation) per 1 L, was prepared, and the pH was adjusted to 6.5 with 1N KOH. Thereafter, the medium was poured into a 300-L jar fermenter, followed by sterilization at 120° C. for 20 minutes. After the medium has been cooled, 450 mL of the aforementioned seed culture was inoculated therein, and maintained at 30° C. The bacterium was precultured for 20 hours with aeration at 113 L/min under a pressure of 50 kPa with agitation at 280 rpm while adjusting the pH to 7.6 with ammonia gas.

Each of the components corresponding to 260 L of the sugar solution, which contains 100 g of glucose and 0.5 g of magnesium sulfate heptahydrate per 1 L, were weighed and dissolved in 50 L, followed by sterilization at 120° C. for 20 minutes. Meanwhile, components of 260 L of the medium, which contains 0.65 g of orthophosphoric acid, 2.9 mL of soybean protein hydrolyzate (total nitrogen content 35 g/L), 1.0 g of ammonium sulfate, 20 mg of ferrous sulfate heptahydrate, 20 mg of manganese sulfate hydrate, 1 mg of D-biotin, 1 mg of thiamine hydrochloride, and 0.05 mL of antifoam (GD-113) per 1 L, were weighed and dissolved in 140 L, and the pH was adjusted to 6.5 with 1N KOH, followed by sterilization at 120° C. for 20 minutes. The sterilized sugar solution and the medium were poured into a 500-L jar fermenter and cooled, and then 70 L of the aforementioned preculture solution was added therein so that the total volume becomes 260 L, followed by incubation at 30° C. The bacterium was cultured for 24 hours with aeration at 113 L/min under a pressure of 50 kPa with agitation at 140 rpm while adjusting the pH to 7.6 with ammonia gas, to thereby prepare bacterial cells having an ability to produce succinic acid. The bacterial cell suspension was concentrated about 4-fold using MF membrane (manufactured by Asahi Kasei Corporation), to thereby prepare a bacterial cell suspension having a dry bacterial cell weight of about 60 g/L. The bacterial cell suspension was stored at 4° C.

(B) Production of Succinic Acid

The bacterial cell suspension was further concentrated by centrifugation, and cells were diluted with the centrifuged supernatant so that the dry bacterial cell weight becomes about 120 g/L. 150 g of glucose and 0.5 g of magnesium sulfate heptahydrate were dissolved in distilled water so that the volume becomes 300 mL, followed by sterilization at 120° C. for 20 minutes. Meanwhile, 0.65 g of orthophosphoric acid, 2.9 mL of soybean protein hydrolyzate (total nitrogen content 35 g/L), 20 mg of ferrous sulfate heptahydrate, 20 mg of manganese sulfate hydrate, 1 mg of D-biotin, 1 mg of thiamine hydrochloride, and 0.05 mL of an antifoam (GD-113) were dissolved in about 300 mL of distilled water, and the pH was adjusted to 6.5 with a 5N potassium hydroxide solution. Thereafter, distilled water was added therein so that the total volume becomes 450 mL, followed by sterilization at 120° C. for 20 minutes. 120 mL of the glucose solution and 180 mL of the medium were mixed and poured into a 1-L jar fermenter, and 100 mL of the aforementioned suspension having a dry bacterial cell weight of about 120 g/L was inoculated therein, followed by incubation at 30° C. The reaction was performed by supplying carbon dioxide at 20 mL/min to the upper surface of the liquid, with agitation at 400 rpm while adjusting the pH to 7.3 with 2.5 M magnesium hydroxide solution, 5 M sodium hydroxide solution, 5M potassium hydroxide solution, and 5 M aqueous ammonia, respectively. The following table shows the succinic acid accumulation, succinic acid production rate, and yield thereof at the time point of 14 hour after the beginning of the reaction.

TABLE 1

| Neutralizing agents | Succinic acid accumulation (g/L) | Succinic acid production rate (g/L/h) | Yield (%) |
|---|---|---|---|
| Magnesium hydroxide | 72.9 | 5.07 | 73.4 |
| Potassium hydroxide | 53.5 | 3.73 | 64.6 |
| Sodium hydroxide | 56.3 | 3.93 | 69.4 |
| Aqueous ammonia | 34.7 | 2.42 | 60.4 |

In the case of the reaction while neutralizing the medium with magnesium hydroxide, the succinic acid accumulation, succinic acid production rate, and yield thereof were significantly higher than those in the case of using potassium hydroxide, sodium hydroxide, or aqueous ammonia.

Example 10

<Reaction While Neutralizing a Medium with Magnesium Carbonate Supplemented with Ammonium Hydrogen Carbonate>

A reaction suspension was prepared in the same way as in Example 7, and ammonium hydrogencarbonate was added thereto so that the final concentration becomes 0.05, 0.1, 0.2, 0.4, and 0.8 mol/L, respectively, and used for reaction. Table 2 shows the sugar consumption rate, succinic acid production rate, and yield thereof at the time point of 20 hour after the beginning of the reaction. It was confirmed that the sugar consumption rate and succinic acid production rate drastically increased by adding an appropriate amount of ammonium hydrogen carbonate in the neutralization reaction together with magnesium carbonate.

TABLE 2

| Ammonium hydrogencarbonate concentration (mol/L) | Sugar consumption rate (g/L/h) | Succinic acid production rate (g/L/h) | Yield (%) |
|---|---|---|---|
| 0 | 2.08 | 1.61 | 77 |
| 0.05 | 3.83 | 2.96 | 77 |
| 0.1 | 5.10 | 3.88 | 76 |
| 0.2 | 6.06 | 4.06 | 67 |
| 0.4 | 6.10 | 4.02 | 66 |
| 0.8 | 4.84 | 2.80 | 58 |

Example 11

<Reaction While Neutralizing a Medium with Magnesium Carbonate Supplemented with Sodium Hydrogen Carbonate (Flask)>

A reaction suspension was prepared in the same way as in Example 7, and sodium hydrogencarbonate was added so that the final concentration becomes 0.05, 0.1, 0.2, 0.4, and 0.8 mol/L, respectively, and used for reaction. Table 3 shows the sugar consumption rate, succinic acid production rate, and yield thereof at the time point of 20 hour after the beginning of the reaction. It was confirmed that the sugar consumption rate, succinic acid production rate, and yield thereof drastically increased by adding an appropriate amount of sodium hydrogen carbonate in the neutralization reaction together with magnesium carbonate.

TABLE 3

| Sodium hydrogen carbonate concentration (mol/L) | Sugar consumption rate (g/L/h) | Succinic acid production rate (g/L/h) | Yield (%) |
|---|---|---|---|
| 0 | 2.08 | 1.61 | 77 |
| 0.05 | 2.30 | 1.83 | 80 |
| 0.1 | 2.37 | 1.98 | 84 |
| 0.2 | 2.67 | 2.18 | 82 |
| 0.4 | 3.17 | 2.67 | 84 |
| 0.8 | 3.77 | 2.72 | 72 |

Example 12

<Reaction While Neutralizing a Medium with Magnesium Carbonate (Jar Fermenter)>

A medium containing 0.2 g of magnesium sulfate heptahydrate, 8 mg of ferrous sulfate heptahydrate, 8 mg of manganese sulfate hydrate, 80 μg of D-biotin, 80 μg of thiamine hydrochloride, 1 mL of antifoam (Adecanol LG294: manufactured by Asahi Denka Co., Ltd.), and dissolved in 200 mL of distilled water was poured into a 500-mL conical flask, followed by sterilization at 120° C. for 20 minutes. The medium was cooled to room temperature, and then it was added to bacterial cells collected from a culture obtained by the same method as Example 7 by centrifugation at 8,000 rpm for 5 minutes to re-suspend the bacterial cells so that O.D. (660 nm) becomes 200. 200 mL of the suspension and 200 mL of 30% glucose solution that had been previously sterilized were poured into a 1-L jar fermenter, and 58.284 g of $4MgCO_3.Mg(OH)_2.5H_2O$ was added and mixed. The reaction suspension was maintained at 35° C., and the reaction was performed with aeration at 100 mL/min, and with agitation at 400 rpm. 16 hours after the beginning of the reaction, most of the glucose was consumed. The sugar consumption rate, succinic acid production rate, and yield thereof were 9.80 g/L/h, 8.78 g/L/h, and 96%, respectively. It was found that the sugar consumption rate, succinic acid production rate, and yield thereof significantly increased by the neutralization reaction with magnesium carbonate in jar culture.

Example 13

<Reaction While Neutralizing a Medium with Magnesium Carbonate Supplemented with Sodium Hydrogen Carbonate (Jar Fermenter)>

A reaction suspension was prepared in the same way as in Example 12, and ammonium hydrogencarbonate was added thereto so that the final concentration becomes 0.1 mol/L, and used for reaction in the same way as described above. 10 hours after the beginning of the reaction, most of the glucose was consumed. The sugar consumption rate, succinic acid production rate, and yield thereof were 15.2 g/L/h, 12.6 g/L/h, and 92%, respectively. It was found that the sugar consumption rate, succinic acid production rate, and yield thereof significantly increased by addition of an appropriate amount of ammonium hydrogen carbonate in jar culture.

Example 14

<Reaction Using Sucrose as Organic Raw Material While Neutralizing a Medium with Magnesium Carbonate (Jar Fermenter)>

A medium containing 0.2 g of magnesium sulfate heptahydrate, 8 mg of ferrous sulfate heptahydrate, 8 mg of manganese sulfate hydrate, 80 μg of D-biotin, 80 μg of thiamine hydrochloride, 1 mL of antifoam (Adecanol LG294: manufactured by Asahi Denka Co., Ltd.), dissolved in 200 mL of distilled water was poured into a 500-mL conical flask, and followed by sterilization at 120° C. for 20 minutes. The medium was cooled to room temperature, and then the medium was added to the bacterial cells collected from the culture obtained by the same method as Example 7 by centrifugation at 8,000 rpm for 5 minutes to re-suspend the bacterial cells so that O.D. (660 nm) becomes 60. 200 mL of the suspension and 200 mL of 20% sucrose solution that had been previously sterilized were poured into a 1-L jar fermenter, and 38.8 g of $4MgCO_3.Mg(OH)_2.5H_2O$ and 3.2 g of ammonium hydrogencarbonate were added and mixed. The reaction suspension was maintained at 35° C., and the reaction was performed with agitation at 400 rpm. About 20 hours after the beginning of the reaction, most of the sucrose was consumed. The sugar consumption rate, succinic acid production rate, and yield thereof were 5 g/L/h, 4.6 g/L/h, and 91%, respectively.

Reference Example 1

<Reaction While Neutralizing a Medium with Ammonium Carbonate (Jar Fermenter)>

100 mL of a medium, which has a composition of 4 g of urea, 14 g of ammonium sulfate, 0.5 g of monobasic potassium phosphate, 0.5 g of dibasic potassium phosphate, 0.5 g of magnesium sulfate heptahydrate, 20 mg of ferrous sulfate heptahydrate, 20 mg of manganese sulfate hydrate, 200 μg of D-biotin, 200 μg of thiamin hydrochloride, 1 g of yeast extract, 1 g of casamino acid, and 1000 mL of distilled water, was poured into a 500-mL conical flask and then sterilized by heat at 120° C. for 20 minutes. The medium was cooled to room temperature and then added with 4 mL of 50% aqueous glucose solution, which had been previously sterilized, and with 50 μL of 5% aqueous kanamycin solution, which had been sterilized by filtration, followed by inoculation of the *Brevibacterium flavum* MJ233/FRD/PC/ΔLDH strain prepared in Example 6(B) to carry out seed culture at 30° C. for 24 hours. A medium containing 12 g of urea, 42 g of ammonium sulfate, 1.5 g of monobasic potassium phosphate, 1.5 g of dibasic potassium phosphate, 1.5 g of magnesium sulfate heptahydrate, 60 mg of ferrous sulfate heptahydrate, 60 mg of manganese sulfate-hydrate, 600 μg of D-biotin, 600 μg of thiamin hydrochloride, 3 g of yeast extract, 3 g of casamino acid, 1 mL of antifoam (Adecanol LG294: manufactured by Asahi Denka Kogyo K.K.), dissolved in 2,500 mL of distilled water was poured into a 5-L fermenter, and then sterilized by heat at 120° C. for 20 minutes. The medium was cooled to room temperature and then added with 500 mL of a 12% aqueous glucose solution, which had been previously sterilized, and the whole amount of the seed culture was added therein, followed by incubation at 30° C. The culture was carried out with aeration at a rate of 500 mL per minute and agitation at a rate of 500 rpm. After 12 hours, the glucose was almost completely consumed.

A medium containing 0.2 g of magnesium sulfate heptahydrate, 8 mg of ferrous sulfate heptahydrate, 8 mg of manganese sulfate-hydrate, 80 μg of D-biotin, 80 μg of thiamin hydrochloride, dissolved in 200 mL of distilled water was poured into a 500-mL conical flask and then sterilized by heat at 120° C. for 20 minutes. After the medium had been cooled to room temperature, the medium was added to the bacterial cells collected from the culture as described above by centrifugation at 8,000 rpm for 5 minutes, to re-suspend the cells so that O.D. (660 nm) becomes 200. 200 ml of the suspension and 200 ml of the previously-sterilized 30% aqueous glucose solution were added to a 1-litter jar fermenter and then maintained at 35° C. The reaction was performed with aeration at a rate of 100 mL per minute and agitation at a rate of 400 rpm while maintaining the pH at 7.6 using 2M ammonium carbonate. About 14 hours after the beginning of the reaction, glucose was almost completely consumed. The glucose consumption rate, succinic acid production rate, and yield thereof were 11 g/L/h, 5.3 g/L/h, and 72%, respectively.

Reference Example 2

<Reaction While Neutralizing a Medium with Sodium Carbonate (Jar Fermenter)>

A reaction suspension was prepared by the same way as in Reference Example 1 described above and the pH was maintained at 7.6 with 2 M sodium carbonate, and the reaction was performed in the same way. About 12 hours after the beginning of the reaction, glucose was almost completely consumed. The glucose consumption rate, succinic acid production rate, and yield thereof were 13 g/L/h, 7.2 g/L/h, and 95%, respectively.

INDUSTRIAL APPLICABILITY

The method of the present invention enables production of a non-amino organic acid while maintaining the pH of an aqueous medium within a certain range without significant increase in the volume of a fermentation reaction solution. Moreover, the method enables significant increase in the production rate or yield of a non-amino organic acid by adding a monovalent cation to an aqueous medium.

The invention claimed is:

1. A method for producing a non-amino organic acid from an organic raw material, comprising reacting bacterial cells or treated bacterial cells of a coryneform bacterium with the organic raw material in an aqueous medium and collecting the non-amino organic acid, wherein the bacterial cells or the treated bacterial cells are allowed to react with the organic raw material while neutralizing the aqueous medium with magnesium carbonate and/or magnesium hydroxide.

2. A method for producing a non-amino organic acid from an organic raw material, comprising reacting bacterial cells or treated bacterial cells of a coryneform bacterium with the organic raw material in an aqueous medium containing a monovalent cation and collecting the non-amino organic acid, wherein the bacterial cells or the treated bacterial cells are allowed to react with the organic raw material while neutralizing the aqueous medium with magnesium carbonate and/or magnesium hydroxide.

3. The method according to claim 2, wherein the monovalent cation is an ammonium ion or a sodium ion.

4. The method according to claim 1, wherein the bacterial cells or the treated bacterial cells are allowed to react with the organic raw material under anaerobic atmosphere.

5. The method according to claim 1, wherein the aqueous medium comprises a carbonate ion, a bicarbonate ion, or carbon dioxide gas.

6. The method according to claim 1, wherein the organic raw material is glucose or sucrose.

7. The method according to claim 1, wherein the non-amino organic acid is succinic acid, malic acid, or fumaric acid.

8. The method according to claim 1, wherein the coryneform bacterium is modified to decrease a lactate dehydrogenase activity to not more than 10% as compared to an unmodified strain.

9. The method according to claim 1, wherein the coryneform bacterium is modified to enhance an activity of fumarate reductase and/or pyruvate carboxylase.

10. The method according to claim 1, wherein the coryneform bacterium is modified to decrease a lactate dehydrogenase activity to not more than 10% as compared to an unmodified strain and enhance an activity of fumarate reductase and/or pyruvate carboxylase.

* * * * *

SEQUENCE LISTING

```
<160> NUMBER OF SEQ ID NOS: 25

<210> SEQ ID NO 1
<211> LENGTH: 34
<212> TYPE: DNA
<213> ORGANISM: Artificial
<220> FEATURE:
<223> OTHER INFORMATION: primer

<400> SEQUENCE: 1

ccttttaac ccatcacata tacctgccgt tcac                                34


<210> SEQ ID NO 2
<211> LENGTH: 32
<212> TYPE: DNA
<213> ORGANISM: Artificial
<220> FEATURE:
<223> OTHER INFORMATION: primer

<400> SEQUENCE: 2

aaaggttagg aatacggtta gccatttgcc tg                                32


<210> SEQ ID NO 3
<211> LENGTH: 21
<212> TYPE: DNA
<213> ORGANISM: Artificial
<220> FEATURE:
<223> OTHER INFORMATION: primer

<400> SEQUENCE: 3

gaggtctgcc tcgtgaagaa g                                            21


<210> SEQ ID NO 4
<211> LENGTH: 27
<212> TYPE: DNA
<213> ORGANISM: Artificial
<220> FEATURE:
<223> OTHER INFORMATION: primer

<400> SEQUENCE: 4

ctcattagaa aaactcatcg agcatca                                      27


<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
```

-continued cgatgaaaga aaccgtcggc 20

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
cgtcagaaga actgcttctg 20

<210> SEQ ID NO 7
<211> LENGTH: 23
<212> TYPE: DNA
<213> ORGANISM: Artificial
<220> FEATURE:
<223> OTHER INFORMATION: primer

<400> SEQUENCE: 7
agttgcatac gcatacgcac tga 23

<210> SEQ ID NO 8
<211> LENGTH: 23
<212> TYPE: DNA
<213> ORGANISM: Artificial
<220> FEATURE:
<223> OTHER INFORMATION: primer

<400> SEQUENCE: 8
gagactggga ctgcaacgtc ttg 23

<210> SEQ ID NO 9
<211> LENGTH: 24
<212> TYPE: DNA
<213> ORGANISM: Artificial
<220> FEATURE:
<223> OTHER INFORMATION: primer

<400> SEQUENCE: 9
gatctttcag ctgctcacac gtga 24

<210> SEQ ID NO 10
<211> LENGTH: 27
<212> TYPE: DNA
<213> ORGANISM: Artificial
<220> FEATURE:
<223> OTHER INFORMATION: primer

<400> SEQUENCE: 10
gatcttaggt cactaaaact aattcag 27

<210> SEQ ID NO 11
<211> LENGTH: 39
<212> TYPE: DNA
<213> ORGANISM: Artificial
<220> FEATURE:
<223> OTHER INFORMATION: primer

<400> SEQUENCE: 11
gatccaggag gcattaatta agcggccgcg ggccctgca 39

<210> SEQ ID NO 12
<211> LENGTH: 31
<212> TYPE: DNA
<213> ORGANISM: Artificial

-continued

```
<220> FEATURE:
<223> OTHER INFORMATION: primer

<400> SEQUENCE: 12

gggcccgcgg ccgcttaatt aatgcctcct g                                31


<210> SEQ ID NO 13
<211> LENGTH: 43
<212> TYPE: DNA
<213> ORGANISM: Artificial
<220> FEATURE:
<223> OTHER INFORMATION: primer

<400> SEQUENCE: 13

accttaatta atgtcgactc acacatcttc aacgcttcca gca                   43


<210> SEQ ID NO 14
<211> LENGTH: 44
<212> TYPE: DNA
<213> ORGANISM: Artificial
<220> FEATURE:
<223> OTHER INFORMATION: primer

<400> SEQUENCE: 14

gttgggccca ggtttaggaa acgacgacga tcaagtcgcc acct                  44


<210> SEQ ID NO 15
<211> LENGTH: 3423
<212> TYPE: DNA
<213> ORGANISM: Brevibacterium flavum
<220> FEATURE:
<221> NAME/KEY: CDS
<222> LOCATION: (1)..(3420)
<223> OTHER INFORMATION:

<400> SEQUENCE: 15

atg tcg act cac aca tct tca acg ctt cca gca ttc aaa aag atc ttg      48
Met Ser Thr His Thr Ser Ser Thr Leu Pro Ala Phe Lys Lys Ile Leu
1               5                   10                  15

gta gca aac cgc ggc gaa atc gcg gtc cgt gct ttc cgt gca gca ctc      96
Val Ala Asn Arg Gly Glu Ile Ala Val Arg Ala Phe Arg Ala Ala Leu
            20                  25                  30

gaa acc ggt gca gcc acg gta gct att tac ccc cgt gaa gat cgg gga     144
Glu Thr Gly Ala Ala Thr Val Ala Ile Tyr Pro Arg Glu Asp Arg Gly
        35                  40                  45

tca ttc cac cgc tct ttt gct tct gaa gct gtc cgc att ggt act gaa     192
Ser Phe His Arg Ser Phe Ala Ser Glu Ala Val Arg Ile Gly Thr Glu
    50                  55                  60

ggc tca cca gtc aag gcg tac ctg gac atc gat gaa att atc ggt gca     240
Gly Ser Pro Val Lys Ala Tyr Leu Asp Ile Asp Glu Ile Ile Gly Ala
65                  70                  75                  80

gct aaa aaa gtt aaa gca gat gct att tac ccg gga tat ggc ttc ctg     288
Ala Lys Lys Val Lys Ala Asp Ala Ile Tyr Pro Gly Tyr Gly Phe Leu
                85                  90                  95

tct gaa aat gcc cag ctt gcc cgc gag tgc gcg gaa aac ggc att act     336
Ser Glu Asn Ala Gln Leu Ala Arg Glu Cys Ala Glu Asn Gly Ile Thr
            100                 105                 110

ttt att ggc cca acc cca gag gtt ctt gat ctc acc ggt gat aag tct     384
Phe Ile Gly Pro Thr Pro Glu Val Leu Asp Leu Thr Gly Asp Lys Ser
        115                 120                 125

cgt gcg gta acc gcc gcg aag aag gct ggt ctg cca gtt ttg gcg gaa     432
Arg Ala Val Thr Ala Ala Lys Lys Ala Gly Leu Pro Val Leu Ala Glu
    130                 135                 140
```

-continued

```
tcc acc ccg agc aaa aac atc gat gac atc gtt aaa agc gct gaa ggc      480
Ser Thr Pro Ser Lys Asn Ile Asp Asp Ile Val Lys Ser Ala Glu Gly
145                 150                 155                 160

cag act tac ccc atc ttt gta aag gca gtt gcc ggt ggt ggc gga cgc      528
Gln Thr Tyr Pro Ile Phe Val Lys Ala Val Ala Gly Gly Gly Gly Arg
                165                 170                 175

ggt atg cgc ttt gtt tct tca cct gat gag ctt cgc aaa ttg gca aca      576
Gly Met Arg Phe Val Ser Ser Pro Asp Glu Leu Arg Lys Leu Ala Thr
            180                 185                 190

gaa gca tct cgt gaa gct gaa gcg gca ttc ggc gac ggt tcg gta tat      624
Glu Ala Ser Arg Glu Ala Glu Ala Ala Phe Gly Asp Gly Ser Val Tyr
        195                 200                 205

gtc gag cgt gct gtg att aac ccc cag cac att gaa gtg cag atc ctt      672
Val Glu Arg Ala Val Ile Asn Pro Gln His Ile Glu Val Gln Ile Leu
    210                 215                 220

ggc gat cgc act gga gaa gtt gta cac ctt tat gaa cgt gac tgc tca      720
Gly Asp Arg Thr Gly Glu Val Val His Leu Tyr Glu Arg Asp Cys Ser
225                 230                 235                 240

ctg cag cgt cgt cac caa aaa gtt gtc gaa att gcg cca gca cag cat      768
Leu Gln Arg Arg His Gln Lys Val Val Glu Ile Ala Pro Ala Gln His
                245                 250                 255

ttg gat cca gaa ctg cgt gat cgc att tgt gcg gat gca gta aag ttc      816
Leu Asp Pro Glu Leu Arg Asp Arg Ile Cys Ala Asp Ala Val Lys Phe
            260                 265                 270

tgc cgc tcc att ggt tac cag ggc gcg gga act gtg gaa ttc ttg gtc      864
Cys Arg Ser Ile Gly Tyr Gln Gly Ala Gly Thr Val Glu Phe Leu Val
        275                 280                 285

gat gaa aag ggc aac cac gtt ttc atc gaa atg aac cca cgt atc cag      912
Asp Glu Lys Gly Asn His Val Phe Ile Glu Met Asn Pro Arg Ile Gln
    290                 295                 300

gtt gag cac acc gtg act gaa gaa gtc acc gag gtg gac ctg gtg aag      960
Val Glu His Thr Val Thr Glu Glu Val Thr Glu Val Asp Leu Val Lys
305                 310                 315                 320

gcg cag atg cgc ttg gct gct ggt gca acc ttg aag gaa ttg ggt ctg     1008
Ala Gln Met Arg Leu Ala Ala Gly Ala Thr Leu Lys Glu Leu Gly Leu
                325                 330                 335

acc caa gat aag atc aag acc cac ggt gcg gca ctg cag tgc cgc atc     1056
Thr Gln Asp Lys Ile Lys Thr His Gly Ala Ala Leu Gln Cys Arg Ile
            340                 345                 350

acc acg gaa gat cca aac aac ggc ttc cgc cca gat acc gga act atc     1104
Thr Thr Glu Asp Pro Asn Asn Gly Phe Arg Pro Asp Thr Gly Thr Ile
        355                 360                 365

acc gcg tac cgc tca cca ggc gga gct ggc gtt cgt ctt gac ggt gca     1152
Thr Ala Tyr Arg Ser Pro Gly Gly Ala Gly Val Arg Leu Asp Gly Ala
    370                 375                 380

gct cag ctc ggt ggc gaa atc acc gca cac ttt gac tcc atg ctg gtg     1200
Ala Gln Leu Gly Gly Glu Ile Thr Ala His Phe Asp Ser Met Leu Val
385                 390                 395                 400

aaa atg acc tgc cgt ggt tcc gat ttt gaa act gct gtt gct cgt gca     1248
Lys Met Thr Cys Arg Gly Ser Asp Phe Glu Thr Ala Val Ala Arg Ala
                405                 410                 415

cag cgc gcg ttg gct gag ttc acc gtg tct ggt gtt gca acc aac att     1296
Gln Arg Ala Leu Ala Glu Phe Thr Val Ser Gly Val Ala Thr Asn Ile
            420                 425                 430

ggt ttc ttg cgt gcg ttg ctg cgt gaa gag gac ttt act tcc aag cgc     1344
Gly Phe Leu Arg Ala Leu Leu Arg Glu Glu Asp Phe Thr Ser Lys Arg
        435                 440                 445

atc gcc acc gga ttt atc ggc gat cac cca cac ctc ctt cag gct cca     1392
Ile Ala Thr Gly Phe Ile Gly Asp His Pro His Leu Leu Gln Ala Pro
    450                 455                 460
```

-continued

```
cct gcg gat gat gag cag gga cgc atc ctg gat tac ttg gca gat gtc     1440
Pro Ala Asp Asp Glu Gln Gly Arg Ile Leu Asp Tyr Leu Ala Asp Val
465                 470                 475                 480

acc gtg aac aag cct cat ggt gtg cgt cca aag gat gtt gca gca cca     1488
Thr Val Asn Lys Pro His Gly Val Arg Pro Lys Asp Val Ala Ala Pro
                485                 490                 495

atc gat aag ctg ccc aac atc aag gat ctg cca ctg cca cgc ggt tcc     1536
Ile Asp Lys Leu Pro Asn Ile Lys Asp Leu Pro Leu Pro Arg Gly Ser
            500                 505                 510

cgt gac cgc ctg aag cag ctt gga cca gca gcg ttt gcc cgc gat ctc     1584
Arg Asp Arg Leu Lys Gln Leu Gly Pro Ala Ala Phe Ala Arg Asp Leu
        515                 520                 525

cgt gag cag gac gca ctg gca gtt act gat acc acc ttc cgc gat gca     1632
Arg Glu Gln Asp Ala Leu Ala Val Thr Asp Thr Thr Phe Arg Asp Ala
    530                 535                 540

cac cag tct ttg ctt gcg acc cga gtc cgc tca ttc gca ctg aag cct     1680
His Gln Ser Leu Leu Ala Thr Arg Val Arg Ser Phe Ala Leu Lys Pro
545                 550                 555                 560

gcg gca gag gcc gtc gca aag ctg act cct gag ctt ttg tcc gtg gag     1728
Ala Ala Glu Ala Val Ala Lys Leu Thr Pro Glu Leu Leu Ser Val Glu
                565                 570                 575

gcc tgg ggc ggt gcg acc tac gat gtg gcg atg cgt ttc ctc ttt gag     1776
Ala Trp Gly Gly Ala Thr Tyr Asp Val Ala Met Arg Phe Leu Phe Glu
            580                 585                 590

gat ccg tgg gac agg ctc gac gag ctg cgc gag gcg atg ccg aat gtg     1824
Asp Pro Trp Asp Arg Leu Asp Glu Leu Arg Glu Ala Met Pro Asn Val
        595                 600                 605

aac att cag atg ctg ctt cgc ggc cgc aac acc gtg gga tac acc cca     1872
Asn Ile Gln Met Leu Leu Arg Gly Arg Asn Thr Val Gly Tyr Thr Pro
    610                 615                 620

tac cca gac tcc gtc tgt cgc gcg ttt gtt aag gaa gct gcc acc tcc     1920
Tyr Pro Asp Ser Val Cys Arg Ala Phe Val Lys Glu Ala Ala Thr Ser
625                 630                 635                 640

ggc gtg gac atc ttc cgc atc ttc gac gcg ctt aac gac gtc tcc cag     1968
Gly Val Asp Ile Phe Arg Ile Phe Asp Ala Leu Asn Asp Val Ser Gln
                645                 650                 655

atg cgt cca gca atc gac gca gtc ctg gag acc aac acc gcg gtc gct     2016
Met Arg Pro Ala Ile Asp Ala Val Leu Glu Thr Asn Thr Ala Val Ala
            660                 665                 670

gaa gtg gct atg gct tat tct ggt gat ctt tcc gat ccg aat gaa aag     2064
Glu Val Ala Met Ala Tyr Ser Gly Asp Leu Ser Asp Pro Asn Glu Lys
        675                 680                 685

ctc tac acc ctg gat tac tac ctg aag atg gca gag gag atc gtc aag     2112
Leu Tyr Thr Leu Asp Tyr Tyr Leu Lys Met Ala Glu Glu Ile Val Lys
    690                 695                 700

tct ggc gct cac att ctg gct att aag gat atg gct ggt ctg ctt cgc     2160
Ser Gly Ala His Ile Leu Ala Ile Lys Asp Met Ala Gly Leu Leu Arg
705                 710                 715                 720

cca gct gca gcc acc aag ctg gtc acc gca ctg cgc cgt gaa ttt gat     2208
Pro Ala Ala Ala Thr Lys Leu Val Thr Ala Leu Arg Arg Glu Phe Asp
                725                 730                 735

ctg cca gtg cac gtg cac acc cac gac act gcg ggt ggc cag ctg gca     2256
Leu Pro Val His Val His Thr His Asp Thr Ala Gly Gly Gln Leu Ala
            740                 745                 750

acc tac ttt gct gca gct caa gct ggt gca gat gct gtt gac ggt gct     2304
Thr Tyr Phe Ala Ala Ala Gln Ala Gly Ala Asp Ala Val Asp Gly Ala
        755                 760                 765

tcc gca cca ctg tct ggc acc acc tcc cag cca tcc ctg tct gcc att     2352
Ser Ala Pro Leu Ser Gly Thr Thr Ser Gln Pro Ser Leu Ser Ala Ile
```

-continued

```
    770                 775                 780

gtt gct gca ttc gcg cac acc cgt cgc gat acc ggt ttg agc ctc gag      2400
Val Ala Ala Phe Ala His Thr Arg Arg Asp Thr Gly Leu Ser Leu Glu
785                 790                 795                 800

gct gtt tct gac ctc gag cca tac tgg gaa gca gtg cgc gga ctg tac      2448
Ala Val Ser Asp Leu Glu Pro Tyr Trp Glu Ala Val Arg Gly Leu Tyr
                805                 810                 815

ctg cca ttt gag tct gga acc cca ggc cca acc ggt cgc gtc tac cgc      2496
Leu Pro Phe Glu Ser Gly Thr Pro Gly Pro Thr Gly Arg Val Tyr Arg
            820                 825                 830

cac gaa atc cca ggc gga cag ctg tcc aac ctg cgt gca cag gcc acc      2544
His Glu Ile Pro Gly Gly Gln Leu Ser Asn Leu Arg Ala Gln Ala Thr
        835                 840                 845

gca ctg ggc ctt gcg gat cgt ttc gaa ctc atc gaa gac aac tac gcg      2592
Ala Leu Gly Leu Ala Asp Arg Phe Glu Leu Ile Glu Asp Asn Tyr Ala
    850                 855                 860

gca gtt aat gag atg ctg gga cgc cca acc aag gtc acc cca tcc tcc      2640
Ala Val Asn Glu Met Leu Gly Arg Pro Thr Lys Val Thr Pro Ser Ser
865                 870                 875                 880

aag gtt gtt ggc gac ctc gca ctc cac ctc gtt ggt gcg ggt gtg gat      2688
Lys Val Val Gly Asp Leu Ala Leu His Leu Val Gly Ala Gly Val Asp
                885                 890                 895

cca gca gac ttt gct gca gat cca caa aag tac gac atc cca gac tct      2736
Pro Ala Asp Phe Ala Ala Asp Pro Gln Lys Tyr Asp Ile Pro Asp Ser
            900                 905                 910

gtc atc gcg ttc ctg cgc ggc gag ctt ggt aac cct cca ggt ggc tgg      2784
Val Ile Ala Phe Leu Arg Gly Glu Leu Gly Asn Pro Pro Gly Gly Trp
        915                 920                 925

cca gag cca ctg cgc acc cgc gca ctg gaa ggc cgc tcc gaa ggc aag      2832
Pro Glu Pro Leu Arg Thr Arg Ala Leu Glu Gly Arg Ser Glu Gly Lys
    930                 935                 940

gca cct ctg acg gaa gtt cct gag gaa gag cag gcg cac ctc gac gct      2880
Ala Pro Leu Thr Glu Val Pro Glu Glu Glu Gln Ala His Leu Asp Ala
945                 950                 955                 960

gat gat tcc aag gaa cgt cgc aac agc ctc aac cgc ctg ctg ttc ccg      2928
Asp Asp Ser Lys Glu Arg Arg Asn Ser Leu Asn Arg Leu Leu Phe Pro
                965                 970                 975

aag cca acc gaa gag ttc ctc gag cac cgt cgc cgc ttc ggc aac acc      2976
Lys Pro Thr Glu Glu Phe Leu Glu His Arg Arg Arg Phe Gly Asn Thr
            980                 985                 990

tct gcg ctg gat gat cgt gaa ttc  ttc tac ggc ctg gtc  gaa ggc cgc    3024
Ser Ala Leu Asp Asp Arg Glu Phe  Phe Tyr Gly Leu Val  Glu Gly Arg
        995                 1000                1005

gag act  ttg atc cgc ctg cca  gat gtg cgc acc cca  ctg ctt gtt      3069
Glu Thr  Leu Ile Arg Leu Pro  Asp Val Arg Thr Pro  Leu Leu Val
    1010                1015                1020

cgc ctg  gat gcg atc tcc gag  cca gac gat aag ggt  atg cgc aat      3114
Arg Leu  Asp Ala Ile Ser Glu  Pro Asp Asp Lys Gly  Met Arg Asn
    1025                1030                1035

gtt gtg  gcc aac gtc aac ggc  cag atc cgc cca atg  cgt gtg cgt      3159
Val Val  Ala Asn Val Asn Gly  Gln Ile Arg Pro Met  Arg Val Arg
    1040                1045                1050

gac cgc  tcc gtt gag tct gtc  acc gca acc gca gaa  aag gca gat      3204
Asp Arg  Ser Val Glu Ser Val  Thr Ala Thr Ala Glu  Lys Ala Asp
    1055                1060                1065

tcc tcc  aac aag ggc cat gtt  gct gca cca ttc gct  ggt gtt gtc      3249
Ser Ser  Asn Lys Gly His Val  Ala Ala Pro Phe Ala  Gly Val Val
    1070                1075                1080

act gtg  act gtt gct gaa ggt  gat gag gtc aag gct  gga gat gca      3294
```

-continued

```
Thr Val  Thr Val Ala Glu Gly  Asp Glu Val Lys Ala  Gly Asp Ala
    1085                 1090                 1095

gtc gca  atc atc gag gct atg  aag atg gaa gca aca  atc act gct      3339
Val Ala  Ile Ile Glu Ala Met  Lys Met Glu Ala Thr  Ile Thr Ala
    1100                 1105                 1110

tct gtt  gac ggc aaa atc gat  cgc gtt gtg gtt cct  gct gca acg      3384
Ser Val  Asp Gly Lys Ile Asp  Arg Val Val Val Pro  Ala Ala Thr
    1115                 1120                 1125

aag gtg  gaa ggt ggc gac ttg  atc gtc gtc gtt tcc  taa              3423
Lys Val  Glu Gly Gly Asp Leu  Ile Val Val Val Ser
    1130                 1135                 1140


<210> SEQ ID NO 16
<211> LENGTH: 1140
<212> TYPE: PRT
<213> ORGANISM: Brevibacterium flavum

<400> SEQUENCE: 16

Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Asp Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ser Ser Pro Asp Glu Leu Arg Lys Leu Ala Thr
            180                 185                 190

Glu Ala Ser Arg Glu Ala Glu Ala Ala Phe Gly Asp Gly Ser Val Tyr
        195                 200                 205

Val Glu Arg Ala Val Ile Asn Pro Gln His Ile Glu Val Gln Ile Leu
    210                 215                 220

Gly Asp Arg Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
    290                 295                 300
```

-continued

```
Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
        355                 360                 365

Thr Ala Tyr Arg Ser Pro Gly Gly Ala Gly Val Arg Leu Asp Gly Ala
    370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
            420                 425                 430

Gly Phe Leu Arg Ala Leu Leu Arg Glu Glu Asp Phe Thr Ser Lys Arg
        435                 440                 445

Ile Ala Thr Gly Phe Ile Gly Asp His Pro His Leu Leu Gln Ala Pro
    450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
            500                 505                 510

Arg Asp Arg Leu Lys Gln Leu Gly Pro Ala Ala Phe Ala Arg Asp Leu
        515                 520                 525

Arg Glu Gln Asp Ala Leu Ala Val Thr Asp Thr Thr Phe Arg Asp Ala
    530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
            580                 585                 590

Asp Pro Trp Asp Arg Leu Asp Glu Leu Arg Glu Ala Met Pro Asn Val
        595                 600                 605

Asn Ile Gln Met Leu Leu Arg Gly Arg Asn Thr Val Gly Tyr Thr Pro
    610                 615                 620

Tyr Pro Asp Ser Val Cys Arg Ala Phe Val Lys Glu Ala Ala Thr Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
            660                 665                 670

Glu Val Ala Met Ala Tyr Ser Gly Asp Leu Ser Asp Pro Asn Glu Lys
        675                 680                 685

Leu Tyr Thr Leu Asp Tyr Tyr Leu Lys Met Ala Glu Glu Ile Val Lys
    690                 695                 700

Ser Gly Ala His Ile Leu Ala Ile Lys Asp Met Ala Gly Leu Leu Arg
705                 710                 715                 720
```

-continued

```
Pro Ala Ala Ala Thr Lys Leu Val Thr Ala Leu Arg Arg Glu Phe Asp
                725                 730                 735

Leu Pro Val His Val His Thr His Asp Thr Ala Gly Gly Gln Leu Ala
            740                 745                 750

Thr Tyr Phe Ala Ala Ala Gln Ala Gly Ala Asp Ala Val Asp Gly Ala
        755                 760                 765

Ser Ala Pro Leu Ser Gly Thr Thr Ser Gln Pro Ser Leu Ser Ala Ile
    770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Pro Gly Pro Thr Gly Arg Val Tyr Arg
            820                 825                 830

His Glu Ile Pro Gly Gly Gln Leu Ser Asn Leu Arg Ala Gln Ala Thr
        835                 840                 845

Ala Leu Gly Leu Ala Asp Arg Phe Glu Leu Ile Glu Asp Asn Tyr Ala
    850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
            900                 905                 910

Val Ile Ala Phe Leu Arg Gly Glu Leu Gly Asn Pro Pro Gly Gly Trp
        915                 920                 925

Pro Glu Pro Leu Arg Thr Arg Ala Leu Glu Gly Arg Ser Glu Gly Lys
    930                 935                 940

Ala Pro Leu Thr Glu Val Pro Glu Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
            980                 985                 990

Ser Ala Leu Asp Asp Arg Glu Phe  Phe Tyr Gly Leu Val  Glu Gly Arg
        995                 1000                1005

Glu Thr  Leu Ile Arg Leu Pro  Asp Val Arg Thr Pro  Leu Leu Val
    1010                1015                1020

Arg Leu  Asp Ala Ile Ser Glu  Pro Asp Asp Lys Gly  Met Arg Asn
    1025                1030                1035

Val Val  Ala Asn Val Asn Gly  Gln Ile Arg Pro Met  Arg Val Arg
    1040                1045                1050

Asp Arg  Ser Val Glu Ser Val  Thr Ala Thr Ala Glu  Lys Ala Asp
    1055                1060                1065

Ser Ser  Asn Lys Gly His Val  Ala Ala Pro Phe Ala  Gly Val Val
    1070                1075                1080

Thr Val  Thr Val Ala Glu Gly  Asp Glu Val Lys Ala  Gly Asp Ala
    1085                1090                1095

Val Ala  Ile Ile Glu Ala Met  Lys Met Glu Ala Thr  Ile Thr Ala
    1100                1105                1110

Ser Val  Asp Gly Lys Ile Asp  Arg Val Val Val Pro  Ala Ala Thr
    1115                1120                1125

Lys Val  Glu Gly Gly Asp Leu  Ile Val Val Val Ser
```

-continued

```
1130                1135                1140
```

<210> SEQ ID NO 17
<211> LENGTH: 35
<212> TYPE: DNA
<213> ORGANISM: Artificial
<220> FEATURE:
<223> OTHER INFORMATION: primer

<400> SEQUENCE: 17

```
ccacctgcag gactccacga tcggcaaaga aacga                               35
```

<210> SEQ ID NO 18
<211> LENGTH: 39
<212> TYPE: DNA
<213> ORGANISM: Artificial
<220> FEATURE:
<223> OTHER INFORMATION: primer

<400> SEQUENCE: 18

```
ggtatttaaa aaggcgcaga gcgtcgtttt gaacatagg                           39
```

<210> SEQ ID NO 19
<211> LENGTH: 3847
<212> TYPE: DNA
<213> ORGANISM: Escherichia coli
<220> FEATURE:
<221> NAME/KEY: CDS
<222> LOCATION: (440)..(2245)
<223> OTHER INFORMATION:
<220> FEATURE:
<221> NAME/KEY: CDS
<222> LOCATION: (2241)..(2975)
<223> OTHER INFORMATION:
<220> FEATURE:
<221> NAME/KEY: CDS
<222> LOCATION: (2986)..(3381)
<223> OTHER INFORMATION:
<220> FEATURE:
<221> NAME/KEY: CDS
<222> LOCATION: (3392)..(3751)
<223> OTHER INFORMATION:

<400> SEQUENCE: 19

```
ccacctgcag gactccacga tcggcaaaga aacgacggat ctccgccata atcgccgcgc     60

gttttaataa gttaggaatg gatgcgctcg gctgccagga tgccgtttcg ctcatagtta    120

aatctccagt ttttgacaag ggcacgaagt ctactcgcaa cgcgacggcg agacaaattt    180

tacgcaggaa tcaaacagcg gtgggcagtg actaaaaaaa gcacgatctg atggtttagt    240

aattaaatta atcatcttca gtgataattt agccctcttg cgcactaaaa aaatcgatct    300

cgtcaaattt cagacttatc catcagacta tactgttgta cctataaagg agcagtggaa    360

tagcgttcgc agaccgtaac tttcaggtac ttaccctgaa gtacgtggct gtgggataaa    420

aacaatctgg aggaatgtc gtg caa acc ttt caa gcc gat ctt gcc att gta     472
                     Met Gln Thr Phe Gln Ala Asp Leu Ala Ile Val
                     1               5                   10

ggc gcc ggt ggc gcg gga tta cgt gct gca att gct gcc gcg cag gca      520
Gly Ala Gly Gly Ala Gly Leu Arg Ala Ala Ile Ala Ala Ala Gln Ala
            15                  20                  25

aat ccg aat gca aaa atc gca cta atc tca aaa gta tac ccg atg cgt      568
Asn Pro Asn Ala Lys Ile Ala Leu Ile Ser Lys Val Tyr Pro Met Arg
        30                  35                  40

agc cat acc gtt gct gca gaa ggg ggc tcc gcc gct gtc gcg cag gat      616
Ser His Thr Val Ala Ala Glu Gly Gly Ser Ala Ala Val Ala Gln Asp
    45                  50                  55
```

-continued

```
cat gac agc ttc gaa tat cac ttt cac gat aca gta gcg ggt ggc gac      664
His Asp Ser Phe Glu Tyr His Phe His Asp Thr Val Ala Gly Gly Asp
60                  65                  70                  75

tgg ttg tgt gag cag gat gtc gtg gat tat ttc gtc cac cac tgc cca      712
Trp Leu Cys Glu Gln Asp Val Val Asp Tyr Phe Val His His Cys Pro
                80                  85                  90

acc gaa atg acc caa ctg gaa ctg tgg gga tgc cca tgg agc cgt cgc      760
Thr Glu Met Thr Gln Leu Glu Leu Trp Gly Cys Pro Trp Ser Arg Arg
            95                  100                 105

ccg gat ggt agc gtc aac gta cgt cgc ttc ggc ggc atg aaa atc gag      808
Pro Asp Gly Ser Val Asn Val Arg Arg Phe Gly Gly Met Lys Ile Glu
        110                 115                 120

cgc acc tgg ttc gcc gcc gat aag acc ggc ttc cat atg ctg cac acg      856
Arg Thr Trp Phe Ala Ala Asp Lys Thr Gly Phe His Met Leu His Thr
    125                 130                 135

ctg ttc cag acc tct ctg caa ttc ccg cag atc cag cgt ttt gac gaa      904
Leu Phe Gln Thr Ser Leu Gln Phe Pro Gln Ile Gln Arg Phe Asp Glu
140                 145                 150                 155

cat ttc gtg ctg gat att ctg gtt gat gat ggt cat gtt cgc ggc ctg      952
His Phe Val Leu Asp Ile Leu Val Asp Asp Gly His Val Arg Gly Leu
                160                 165                 170

gta gca atg aac atg atg gaa ggc acg ctg gtg cag atc cgt gct aac     1000
Val Ala Met Asn Met Met Glu Gly Thr Leu Val Gln Ile Arg Ala Asn
            175                 180                 185

gcg gtc gtt atg gct act ggc ggt gcg ggt cgc gtt tat cgt tac aac     1048
Ala Val Val Met Ala Thr Gly Gly Ala Gly Arg Val Tyr Arg Tyr Asn
        190                 195                 200

acc aac ggc ggc atc gtt acc ggt gac ggt atg ggt atg gcg cta agc     1096
Thr Asn Gly Gly Ile Val Thr Gly Asp Gly Met Gly Met Ala Leu Ser
    205                 210                 215

cac ggc gtt ccg ctg cgt gac atg gaa ttc gtt cag tat cac cca acc     1144
His Gly Val Pro Leu Arg Asp Met Glu Phe Val Gln Tyr His Pro Thr
220                 225                 230                 235

ggt ctg cca ggt tcc ggt atc ctg atg acc gaa ggt tgc cgc ggt gaa     1192
Gly Leu Pro Gly Ser Gly Ile Leu Met Thr Glu Gly Cys Arg Gly Glu
                240                 245                 250

ggc ggt att ctg gtc aac aaa aat ggc tac cgt tat ctg caa gat tac     1240
Gly Gly Ile Leu Val Asn Lys Asn Gly Tyr Arg Tyr Leu Gln Asp Tyr
            255                 260                 265

ggc atg ggc ccg gaa act ccg ctg ggc gag ccg aaa aac aaa tat atg     1288
Gly Met Gly Pro Glu Thr Pro Leu Gly Glu Pro Lys Asn Lys Tyr Met
        270                 275                 280

gaa ctg ggt cca cgc gac aaa gtc tct cag gcc ttc tgg cac gaa tgg     1336
Glu Leu Gly Pro Arg Asp Lys Val Ser Gln Ala Phe Trp His Glu Trp
    285                 290                 295

cgt aaa ggc aac acc atc tcc acg ccg cgt ggc gat gtg gtt tat ctc     1384
Arg Lys Gly Asn Thr Ile Ser Thr Pro Arg Gly Asp Val Val Tyr Leu
300                 305                 310                 315

gac ttg cgt cac ctc ggc gag aaa aaa ctg cat gaa cgt ctg ccg ttc     1432
Asp Leu Arg His Leu Gly Glu Lys Lys Leu His Glu Arg Leu Pro Phe
                320                 325                 330

atc tgc gaa ctg gcg aaa gcg tac gtt ggc gtc gat ccg gtt aaa gaa     1480
Ile Cys Glu Leu Ala Lys Ala Tyr Val Gly Val Asp Pro Val Lys Glu
            335                 340                 345

ccg att ccg gta cgt ccg acc gca cac tac acc atg ggc ggt atc gaa     1528
Pro Ile Pro Val Arg Pro Thr Ala His Tyr Thr Met Gly Gly Ile Glu
        350                 355                 360

acc gat cag aac tgt gaa acc cgc att aaa ggt ctg ttc gcc gtg ggt     1576
Thr Asp Gln Asn Cys Glu Thr Arg Ile Lys Gly Leu Phe Ala Val Gly
```

-continued

```
    365                 370                 375

gaa tgt tcc tct gtt ggt ctg cac ggt gca aac cgt ctg ggt tct aac     1624
Glu Cys Ser Ser Val Gly Leu His Gly Ala Asn Arg Leu Gly Ser Asn
380                 385                 390                 395

tcc ctg gcg gaa ctg gtg gtc ttc ggc cgt ctg gcc ggt gaa caa gcg     1672
Ser Leu Ala Glu Leu Val Val Phe Gly Arg Leu Ala Gly Glu Gln Ala
                400                 405                 410

aca gag cgt gca gca act gcc ggt aat ggc aac gaa gcg gca att gaa     1720
Thr Glu Arg Ala Ala Thr Ala Gly Asn Gly Asn Glu Ala Ala Ile Glu
            415                 420                 425

gcg cag gca gct ggc gtt gaa caa cgt ctg aaa gat ctg gtt aac cag     1768
Ala Gln Ala Ala Gly Val Glu Gln Arg Leu Lys Asp Leu Val Asn Gln
        430                 435                 440

gat ggc ggc gaa aac tgg gcg aag atc cgc gac gaa atg ggc ctg gct     1816
Asp Gly Gly Glu Asn Trp Ala Lys Ile Arg Asp Glu Met Gly Leu Ala
    445                 450                 455

atg gaa gaa ggc tgc ggt atc tac cgt acg ccg gaa ctg atg cag aaa     1864
Met Glu Glu Gly Cys Gly Ile Tyr Arg Thr Pro Glu Leu Met Gln Lys
460                 465                 470                 475

acc atc gac aag ctg gca gag ctg cag gaa cgc ttc aag cgc gtg cgc     1912
Thr Ile Asp Lys Leu Ala Glu Leu Gln Glu Arg Phe Lys Arg Val Arg
                480                 485                 490

atc acc gac act tcc agc gtg ttc aac acc gac ctg ctc tac acc att     1960
Ile Thr Asp Thr Ser Ser Val Phe Asn Thr Asp Leu Leu Tyr Thr Ile
            495                 500                 505

gaa ctg ggc cac ggt ctg aac gtt gct gaa tgt atg gcg cac tcc gca     2008
Glu Leu Gly His Gly Leu Asn Val Ala Glu Cys Met Ala His Ser Ala
        510                 515                 520

atg gca cgt aaa gag tcc cgc ggc gcg cac cag cgt ctg gac gaa ggt     2056
Met Ala Arg Lys Glu Ser Arg Gly Ala His Gln Arg Leu Asp Glu Gly
    525                 530                 535

tgc acc gag cgt gac gac gtc aac ttc ctc aaa cac acc ctc gcc ttc     2104
Cys Thr Glu Arg Asp Asp Val Asn Phe Leu Lys His Thr Leu Ala Phe
540                 545                 550                 555

cgc gat gct gat ggc acg act cgc ctg gag tac agc gac gtg aag att     2152
Arg Asp Ala Asp Gly Thr Thr Arg Leu Glu Tyr Ser Asp Val Lys Ile
                560                 565                 570

act acg ctg ccg cca gct aaa cgc gtt tac ggt ggc gaa gcg gat gca     2200
Thr Thr Leu Pro Pro Ala Lys Arg Val Tyr Gly Gly Glu Ala Asp Ala
            575                 580                 585

gcc gat aag gcg gaa gca gcc aat aag aag gag aag gcg a atg gct gag   2249
Ala Asp Lys Ala Glu Ala Ala Asn Lys Lys Glu Lys Ala   Met Ala Glu
        590                 595                 600

atg aaa aac ctg aaa att gag gtg gtg cgc tat aac ccg aaa gtc gat     2297
Met Lys Asn Leu Lys Ile Glu Val Val Arg Tyr Asn Pro Lys Val Asp
    605                 610                 615

acc gca ccg cat agc gca ttc tat gaa gtg cct tat gac gca act acc     2345
Thr Ala Pro His Ser Ala Phe Tyr Glu Val Pro Tyr Asp Ala Thr Thr
620                 625                 630                 635

tca tta ctg gat gcg ctg ggc tac atc aaa gac aac ctg gca ccg gac     2393
Ser Leu Leu Asp Ala Leu Gly Tyr Ile Lys Asp Asn Leu Ala Pro Asp
                640                 645                 650

ctg agc tac cgc tgg tcc tgc cgt atg gcg att tgt ggt tcc tgc ggc     2441
Leu Ser Tyr Arg Trp Ser Cys Arg Met Ala Ile Cys Gly Ser Cys Gly
            655                 660                 665

atg atg gtt aac aac gtg cca aaa ctg gca tgt aaa acc ttc ctg cgt     2489
Met Met Val Asn Asn Val Pro Lys Leu Ala Cys Lys Thr Phe Leu Arg
        670                 675                 680

gat tac acc gac ggt atg aag gtt gaa gcg tta gct aac ttc ccg att     2537
```

-continued

```
Asp Tyr Thr Asp Gly Met Lys Val Glu Ala Leu Ala Asn Phe Pro Ile
    685                 690                 695

gaa cgc gat ctg gtg gtc gat atg acc cac ttc atc gaa agt ctg gaa      2585
Glu Arg Asp Leu Val Val Asp Met Thr His Phe Ile Glu Ser Leu Glu
700                 705                 710                 715

gcg atc aaa ccg tac atc atc ggc aac tcc cgc acc gcg gat cag ggt      2633
Ala Ile Lys Pro Tyr Ile Ile Gly Asn Ser Arg Thr Ala Asp Gln Gly
                720                 725                 730

act aac atc cag acc ccg gcg cag atg gcg aag tat cac cag ttc tcc      2681
Thr Asn Ile Gln Thr Pro Ala Gln Met Ala Lys Tyr His Gln Phe Ser
            735                 740                 745

ggt tgc atc aac tgt ggt ttg tgc tac gcc gcg tgc ccg cag ttt ggc      2729
Gly Cys Ile Asn Cys Gly Leu Cys Tyr Ala Ala Cys Pro Gln Phe Gly
        750                 755                 760

ctg aac cca gag ttc atc ggt ccg gct gcc att acg ctg gcg cat cgt      2777
Leu Asn Pro Glu Phe Ile Gly Pro Ala Ala Ile Thr Leu Ala His Arg
    765                 770                 775

tat aac gaa gat agc cgc gac cac ggt aag aag gag cgt atg gcg cag      2825
Tyr Asn Glu Asp Ser Arg Asp His Gly Lys Lys Glu Arg Met Ala Gln
780                 785                 790                 795

ttg aac agc cag aac ggc gta tgg agc tgt act ttc gtg ggc tac tgc      2873
Leu Asn Ser Gln Asn Gly Val Trp Ser Cys Thr Phe Val Gly Tyr Cys
                800                 805                 810

tcc gaa gtc tgc ccg aaa cac gtc gat ccg gct gcg gcc att cag cag      2921
Ser Glu Val Cys Pro Lys His Val Asp Pro Ala Ala Ala Ile Gln Gln
            815                 820                 825

ggc aaa gta gaa agt tcg aaa gac ttt ctt atc gcg acc ctg aaa cca      2969
Gly Lys Val Glu Ser Ser Lys Asp Phe Leu Ile Ala Thr Leu Lys Pro
        830                 835                 840

cgc taa ggagtgcaac atg acg act aaa cgt aaa ccg tat gta cgg cca      3018
Arg                Met Thr Thr Lys Arg Lys Pro Tyr Val Arg Pro
                   845                 850                 855

atg acg tcc acc tgg tgg aaa aaa ttg ccg ttt tat cgc ttt tac atg      3066
Met Thr Ser Thr Trp Trp Lys Lys Leu Pro Phe Tyr Arg Phe Tyr Met
                860                 865                 870

ctg cgc gaa ggc acg gcg gtt ccg gct gtg tgg ttc agc att gaa ctg      3114
Leu Arg Glu Gly Thr Ala Val Pro Ala Val Trp Phe Ser Ile Glu Leu
            875                 880                 885

att ttc ggg ctg ttt gcc ctg aaa aat ggc ccg gaa gcc tgg gcg gga      3162
Ile Phe Gly Leu Phe Ala Leu Lys Asn Gly Pro Glu Ala Trp Ala Gly
        890                 895                 900

ttc gtc gac ttt tta caa aac ccg gtt atc gtg atc att aac ctg atc      3210
Phe Val Asp Phe Leu Gln Asn Pro Val Ile Val Ile Ile Asn Leu Ile
    905                 910                 915

act ctg gcg gca gct ctg ctg cac acc aaa acc tgg ttt gaa ctg gca      3258
Thr Leu Ala Ala Ala Leu Leu His Thr Lys Thr Trp Phe Glu Leu Ala
920                 925                 930                 935

ccg aaa gcg gcc aat atc att gta aaa gac gaa aaa atg gga cca gag      3306
Pro Lys Ala Ala Asn Ile Ile Val Lys Asp Glu Lys Met Gly Pro Glu
                940                 945                 950

cca att atc aaa agt ctc tgg gcg gta act gtg gtt gcc acc atc gta      3354
Pro Ile Ile Lys Ser Leu Trp Ala Val Thr Val Val Ala Thr Ile Val
            955                 960                 965

atc ctg ttt gtt gcc ctg tac tgg taa ggagcctgag atg att aat cca      3403
Ile Leu Phe Val Ala Leu Tyr Trp                Met Ile Asn Pro
        970                 975

aat cca aag cgt tct gac gaa ccg gta ttc tgg ggc ctc ttc ggg gcc      3451
Asn Pro Lys Arg Ser Asp Glu Pro Val Phe Trp Gly Leu Phe Gly Ala
980                 985                 990                 995
```

-continued

```
ggt ggt atg tgg agc  gcc atc att gcg ccg  gtg atg atc ctg ctg       3496
Gly Gly Met Trp Ser  Ala Ile Ile Ala Pro  Val Met Ile Leu Leu
                1000                 1005                 1010

gtg ggt att ctg ctg  cca ctg ggg ttg ttt  ccg ggt gat gcg ctg       3541
Val Gly Ile Leu Leu  Pro Leu Gly Leu Phe  Pro Gly Asp Ala Leu
                1015                 1020                 1025

agc tac gag cgc gtt  ctg gcg ttc gcg cag  agc ttc att ggt cgc       3586
Ser Tyr Glu Arg Val  Leu Ala Phe Ala Gln  Ser Phe Ile Gly Arg
                1030                 1035                 1040

gta ttc ctg ttc ctg  atg atc gtt ctg ccg  ctg tgg tgt ggt tta       3631
Val Phe Leu Phe Leu  Met Ile Val Leu Pro  Leu Trp Cys Gly Leu
                1045                 1050                 1055

cac cgt atg cac cac  gcg atg cac gat ctg  aaa atc cac gta cct       3676
His Arg Met His His  Ala Met His Asp Leu  Lys Ile His Val Pro
                1060                 1065                 1070

gcg ggc aaa tgg gtt  ttc tac ggt ctg gct  gct atc ctg aca gtt       3721
Ala Gly Lys Trp Val  Phe Tyr Gly Leu Ala  Ala Ile Leu Thr Val
                1075                 1080                 1085

gtc acg ctg att ggt  gtc gtt aca atc taa cgcatcgcca atgtaaatcc      3771
Val Thr Leu Ile Gly  Val Val Thr Ile
                1090

ggcccgccta tggcgggccg ttttgtatgg aaaccagacc ctatgttcaa aacgacgctc   3831

tgcgcctttt aatacc                                                   3847


<210> SEQ ID NO 20
<211> LENGTH: 602
<212> TYPE: PRT
<213> ORGANISM: Escherichia coli

<400> SEQUENCE: 20

Met Gln Thr Phe Gln Ala Asp Leu Ala Ile Val Gly Ala Gly Gly Ala
1               5                   10                  15

Gly Leu Arg Ala Ala Ile Ala Ala Ala Gln Ala Asn Pro Asn Ala Lys
            20                  25                  30

Ile Ala Leu Ile Ser Lys Val Tyr Pro Met Arg Ser His Thr Val Ala
        35                  40                  45

Ala Glu Gly Gly Ser Ala Ala Val Ala Gln Asp His Asp Ser Phe Glu
    50                  55                  60

Tyr His Phe His Asp Thr Val Ala Gly Gly Asp Trp Leu Cys Glu Gln
65                  70                  75                  80

Asp Val Val Asp Tyr Phe Val His His Cys Pro Thr Glu Met Thr Gln
                85                  90                  95

Leu Glu Leu Trp Gly Cys Pro Trp Ser Arg Arg Pro Asp Gly Ser Val
            100                 105                 110

Asn Val Arg Arg Phe Gly Gly Met Lys Ile Glu Arg Thr Trp Phe Ala
        115                 120                 125

Ala Asp Lys Thr Gly Phe His Met Leu His Thr Leu Phe Gln Thr Ser
    130                 135                 140

Leu Gln Phe Pro Gln Ile Gln Arg Phe Asp Glu His Phe Val Leu Asp
145                 150                 155                 160

Ile Leu Val Asp Asp Gly His Val Arg Gly Leu Val Ala Met Asn Met
                165                 170                 175

Met Glu Gly Thr Leu Val Gln Ile Arg Ala Asn Ala Val Val Met Ala
            180                 185                 190

Thr Gly Gly Ala Gly Arg Val Tyr Arg Tyr Asn Thr Asn Gly Gly Ile
        195                 200                 205
```

-continued

```
Val Thr Gly Asp Gly Met Gly Met Ala Leu Ser His Gly Val Pro Leu
    210                 215                 220

Arg Asp Met Glu Phe Val Gln Tyr His Pro Thr Gly Leu Pro Gly Ser
225                 230                 235                 240

Gly Ile Leu Met Thr Glu Gly Cys Arg Gly Glu Gly Gly Ile Leu Val
                245                 250                 255

Asn Lys Asn Gly Tyr Arg Tyr Leu Gln Asp Tyr Gly Met Gly Pro Glu
            260                 265                 270

Thr Pro Leu Gly Glu Pro Lys Asn Lys Tyr Met Glu Leu Gly Pro Arg
        275                 280                 285

Asp Lys Val Ser Gln Ala Phe Trp His Glu Trp Arg Lys Gly Asn Thr
    290                 295                 300

Ile Ser Thr Pro Arg Gly Asp Val Val Tyr Leu Asp Leu Arg His Leu
305                 310                 315                 320

Gly Glu Lys Lys Leu His Glu Arg Leu Pro Phe Ile Cys Glu Leu Ala
                325                 330                 335

Lys Ala Tyr Val Gly Val Asp Pro Val Lys Glu Pro Ile Pro Val Arg
            340                 345                 350

Pro Thr Ala His Tyr Thr Met Gly Gly Ile Glu Thr Asp Gln Asn Cys
        355                 360                 365

Glu Thr Arg Ile Lys Gly Leu Phe Ala Val Gly Glu Cys Ser Ser Val
    370                 375                 380

Gly Leu His Gly Ala Asn Arg Leu Gly Ser Asn Ser Leu Ala Glu Leu
385                 390                 395                 400

Val Val Phe Gly Arg Leu Ala Gly Glu Gln Ala Thr Glu Arg Ala Ala
                405                 410                 415

Thr Ala Gly Asn Gly Asn Glu Ala Ala Ile Glu Ala Gln Ala Ala Gly
            420                 425                 430

Val Glu Gln Arg Leu Lys Asp Leu Val Asn Gln Asp Gly Gly Glu Asn
        435                 440                 445

Trp Ala Lys Ile Arg Asp Glu Met Gly Leu Ala Met Glu Glu Gly Cys
    450                 455                 460

Gly Ile Tyr Arg Thr Pro Glu Leu Met Gln Lys Thr Ile Asp Lys Leu
465                 470                 475                 480

Ala Glu Leu Gln Glu Arg Phe Lys Arg Val Arg Ile Thr Asp Thr Ser
                485                 490                 495

Ser Val Phe Asn Thr Asp Leu Leu Tyr Thr Ile Glu Leu Gly His Gly
            500                 505                 510

Leu Asn Val Ala Glu Cys Met Ala His Ser Ala Met Ala Arg Lys Glu
        515                 520                 525

Ser Arg Gly Ala His Gln Arg Leu Asp Glu Gly Cys Thr Glu Arg Asp
    530                 535                 540

Asp Val Asn Phe Leu Lys His Thr Leu Ala Phe Arg Asp Ala Asp Gly
545                 550                 555                 560

Thr Thr Arg Leu Glu Tyr Ser Asp Val Lys Ile Thr Thr Leu Pro Pro
                565                 570                 575

Ala Lys Arg Val Tyr Gly Gly Glu Ala Asp Ala Ala Asp Lys Ala Glu
            580                 585                 590

Ala Ala Asn Lys Lys Glu Lys Ala Asn Gly
        595                 600
```

```
<210> SEQ ID NO 21
<211> LENGTH: 244
<212> TYPE: PRT
```

<213> ORGANISM: Escherichia coli

<400> SEQUENCE: 21

```
Met Ala Glu Met Lys Asn Leu Lys Ile Glu Val Val Arg Tyr Asn Pro
1               5                   10                  15

Lys Val Asp Thr Ala Pro His Ser Ala Phe Tyr Glu Val Pro Tyr Asp
            20                  25                  30

Ala Thr Thr Ser Leu Leu Asp Ala Leu Gly Tyr Ile Lys Asp Asn Leu
        35                  40                  45

Ala Pro Asp Leu Ser Tyr Arg Trp Ser Cys Arg Met Ala Ile Cys Gly
    50                  55                  60

Ser Cys Gly Met Met Val Asn Asn Val Pro Lys Leu Ala Cys Lys Thr
65                  70                  75                  80

Phe Leu Arg Asp Tyr Thr Asp Gly Met Lys Val Glu Ala Leu Ala Asn
                85                  90                  95

Phe Pro Ile Glu Arg Asp Leu Val Val Asp Met Thr His Phe Ile Glu
            100                 105                 110

Ser Leu Glu Ala Ile Lys Pro Tyr Ile Ile Gly Asn Ser Arg Thr Ala
        115                 120                 125

Asp Gln Gly Thr Asn Ile Gln Thr Pro Ala Gln Met Ala Lys Tyr His
    130                 135                 140

Gln Phe Ser Gly Cys Ile Asn Cys Gly Leu Cys Tyr Ala Ala Cys Pro
145                 150                 155                 160

Gln Phe Gly Leu Asn Pro Glu Phe Ile Gly Pro Ala Ala Ile Thr Leu
                165                 170                 175

Ala His Arg Tyr Asn Glu Asp Ser Arg Asp His Gly Lys Lys Glu Arg
            180                 185                 190

Met Ala Gln Leu Asn Ser Gln Asn Gly Val Trp Ser Cys Thr Phe Val
        195                 200                 205

Gly Tyr Cys Ser Glu Val Cys Pro Lys His Val Asp Pro Ala Ala Ala
    210                 215                 220

Ile Gln Gln Gly Lys Val Glu Ser Ser Lys Asp Phe Leu Ile Ala Thr
225                 230                 235                 240

Leu Lys Pro Arg
```

<210> SEQ ID NO 22
<211> LENGTH: 131
<212> TYPE: PRT
<213> ORGANISM: Escherichia coli

<400> SEQUENCE: 22

```
Met Thr Thr Lys Arg Lys Pro Tyr Val Arg Pro Met Thr Ser Thr Trp
1               5                   10                  15

Trp Lys Lys Leu Pro Phe Tyr Arg Phe Tyr Met Leu Arg Glu Gly Thr
            20                  25                  30

Ala Val Pro Ala Val Trp Phe Ser Ile Glu Leu Ile Phe Gly Leu Phe
        35                  40                  45

Ala Leu Lys Asn Gly Pro Glu Ala Trp Ala Gly Phe Val Asp Phe Leu
    50                  55                  60

Gln Asn Pro Val Ile Val Ile Ile Asn Leu Ile Thr Leu Ala Ala Ala
65                  70                  75                  80

Leu Leu His Thr Lys Thr Trp Phe Glu Leu Ala Pro Lys Ala Ala Asn
                85                  90                  95

Ile Ile Val Lys Asp Glu Lys Met Gly Pro Glu Pro Ile Ile Lys Ser
            100                 105                 110
```

-continued

```
Leu Trp Ala Val Thr Val Val Ala Thr Ile Val Ile Leu Phe Val Ala
        115                 120                 125

Leu Tyr Trp
    130


<210> SEQ ID NO 23
<211> LENGTH: 119
<212> TYPE: PRT
<213> ORGANISM: Escherichia coli

<400> SEQUENCE: 23

Met Ile Asn Pro Asn Pro Lys Arg Ser Asp Glu Pro Val Phe Trp Gly
1               5                   10                  15

Leu Phe Gly Ala Gly Gly Met Trp Ser Ala Ile Ile Ala Pro Val Met
            20                  25                  30

Ile Leu Leu Val Gly Ile Leu Leu Pro Leu Gly Leu Phe Pro Gly Asp
        35                  40                  45

Ala Leu Ser Tyr Glu Arg Val Leu Ala Phe Ala Gln Ser Phe Ile Gly
    50                  55                  60

Arg Val Phe Leu Phe Leu Met Ile Val Leu Pro Leu Trp Cys Gly Leu
65                  70                  75                  80

His Arg Met His His Ala Met His Asp Leu Lys Ile His Val Pro Ala
                85                  90                  95

Gly Lys Trp Val Phe Tyr Gly Leu Ala Ala Ile Leu Thr Val Val Thr
            100                 105                 110

Leu Ile Gly Val Val Thr Ile
        115


<210> SEQ ID NO 24
<211> LENGTH: 16
<212> TYPE: DNA
<213> ORGANISM: Artificial
<220> FEATURE:
<223> OTHER INFORMATION: primer

<400> SEQUENCE: 24

atatgaaacc cggtac                                                   16


<210> SEQ ID NO 25
<211> LENGTH: 16
<212> TYPE: DNA
<213> ORGANISM: Artificial
<220> FEATURE:
<223> OTHER INFORMATION: primer

<400> SEQUENCE: 25

cgggtttcat atgtac                                                   16
```